(12) United States Patent
Nantz et al.

(10) Patent No.: US 6,200,599 B1
(45) Date of Patent: Mar. 13, 2001

(54) ORTHO ESTER LIPIDS

(75) Inventors: Michael H. Nantz; Ji Zhu, both of Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/415,016

(22) Filed: Oct. 7, 1999

(51) Int. Cl.[7] .......................... A61K 9/127; C12N 15/00; C12N 15/88
(52) U.S. Cl. .......................... 424/450; 435/440; 435/458
(58) Field of Search .................................. 435/440, 458; 424/450

(56) References Cited

U.S. PATENT DOCUMENTS

| | | | |
|---|---|---|---|
| 4,529,561 | 7/1985 | Hunt et al. | 264/4.3 |
| 4,737,323 | 4/1988 | Martin et al. | 264/4.3 |

OTHER PUBLICATIONS

Victor A. Bloomfield, "Quasi–elastic Light Scattering Applications in Biochemistry and Biology", *Ann. Rev. Biophys. Bioeng.*, 10:421–450 (1981).

Budker, et al., "pH–sensitive, Cationic Liposomes: A New Synthetic Virus–Like Vector", *Nature Biotechnology*, 14:760–764 (Jun. 1996).

Nejat Dünes, et al., "pH–Sensitive Liposomes", *Membrane Fusion*, pp. 713–730 (1990).

Heller, J., "Development of poly(ortho esters): a historical overview", *Biomaterials*, 11:659–665 (Nov. 1990).

Ng, S. Y., et al., "Synthesis and erosion studies of self–catalyzed poly(orthoester)s", *Macromolecules*, 30:770–772 (1997).

Sintzel, et al., "Synthesis and characterization of self–catalyzed poly(ortho ester)", *Biomaterials*, 19:791–800 (1998).

Stribling, Roscoe, et al., "Aerosol gene delivery in vivo," *Proc. Nat'l. Acad. Sci. USA*, vol. 89, pp. 11277–11281.

Szoka, Francis, Jr., et al., "Procedure for preparation of liposomes with large internal aqueous space and high capture by reverse–phase evaporation", *Proc. Natl. Acad. Sci. USA*, vol. 75:9, pp. 4194–4198 (Sep. 1978).

Uster, Paul S., et al,. "pH–Dependent Fusion of Liposomes Using Titratable Polycations," *Biochemistry*, vol. 24:1 (1985).

Wang, Chen–Yen, et al., "Highly Efficient DNA Delivery Mediated by pH–Sensitive Immunoliposomes," *Biochemistry*, 28, 9508–9514 (1989).

Yatvin, M. B., et al., "pH–Sensitive Liposomes: Possible Clinical Implications," *Science*, vol. 210, pp. 1253–1255 (1980).

Zhu, Ning, et al., "Systemic Gene Expression After Intravenous DNA Delivery Into Adult Mice," *Science*, vol. 261, pp. 209–211 (1993).

*Primary Examiner*—Robert A. Schwartzman
*Assistant Examiner*—Andrea Ousley
(74) *Attorney, Agent, or Firm*—Townsend and Townsend and Crew LLP

(57) ABSTRACT

The present invention provides ortho ester lipids and their derivatives that, upon certain pH conditions, undergo hydrolysis with concomitant or subsequent headgroup cleavage. These ortho ester lipids can advantageously be formulated into liposomes. The liposome formulations are useful in nucleic acid transfection and entrapment/delivery of conventional small molecules and therapeutic agents. Moreover, the liposomes comprising compounds of the present invention are useful as drug delivery vehicles.

28 Claims, 11 Drawing Sheets

Ortho Ester Functionality

Compound 10

Step I. Ortho Ester Hydrolysis

Step II. Headgroup Cleavage

Lactone 12        Amino Alcohol 18

Calcein

ORTHO ESTER LIPIDS

FIELD OF THE INVENTION

In general, this invention relates to ortho ester lipids, their derivatives, and their use in liposome formulations, and more particularly, to the use of ortho ester lipids in nucleic acid transfection.

BACKGROUND OF THE INVENTION

In general, amphipathic molecules have distinct regions of hydrophilic character and distinct regions of hydrophobic character. Amphipathic molecules form three types of macromolecular structures when dispersed in water: micelles, hexagonal phase and lipid bilayers. The exact macromolecular structure depends in part, to the relative sizes of the hydrophilic and hydrophobic regions of the molecule.

In certain instances, when the cross-sectional area of the hydrophilic region of the molecule is slightly less than, or equal to, that of the hydrophobic part of the molecule, such as in many phospholipids, the formation of bilayers is favored. Phospholipids contain one phosphate, a glycerol and one or more fatty acids. These molecules form lipid bilayers that are two-dimensional sheets in which all of the hydrophobic portions, e.g., acyl side chains, are shielded from interaction with water except those at the ends of the sheet. These bilayers form three-dimensional vesicles known as liposomes.

Liposomes are self-assembling structures comprising one or more bilayers of amphipathic lipid molecules that enclose an internal aqueous volume. The amphipathic lipid molecules that make up the lipid bilayers comprise a polar headgroup region covalently linked to one or two non-polar acyl chains. In certain instances, the energetically unfavorable contact between the hydrophobic acyl chains and the aqueous solution surrounding the lipid molecules causes them to rearrange and thus, the polar headgroups are oriented towards the aqueous solution, while the acyl chains orient towards the interior part of the bilayer. The lipid bilayer structure comprises two opposing monolayers, wherein the acyl chains are shielded from coming into contact with the surrounding medium.

Liposomes are excellent vehicles for drug delivery. In a liposome-drug delivery system, an active ingredient, such as a drug, is encapsulated or entrapped in the liposome and then administered to the patient to be treated. Alternatively, if the active ingredient is lipophilic, it may associate with the lipid bilayer. Active ingredients entrapped within liposomes can reduce toxicity, increase efficacy, or both.

One area of liposome research has been the design of the "trigger" for the liposome to release its payload or active agent. Various parameters to initiate release can be used, which include pH, ionic strength, controlled release and antibody attachment. Past developments of pH-sensitive liposomes have focused principally in the area of anionic liposomes comprised largely of phosphatidylethanolamine (PE) bilayers (see, Huang et al., *Biochemistry*, 28, 9508–9514 (1989); Duzgunes et al., *pH-Sensitive Liposomes*, in *Membrane Fusion* 1990, pp. 713–730; Wilschut, J. and Hoekstra, D. (eds.), Marcel-Decker Inc., New York. and Yatvin et al., *Science*, 210, 1253–1255 (1980)). The addition of lipids containing carboxylate groups (e.g., hemisuccinate, oleic acid, etc.) to PE lipids help stabilize bilayer morphology at nonacidic pH. After cellular internalization occurs via endocytosis of PE liposome preparations containing carboxylate lipids, endosomal acidification progresses. As the acidification progresses below the pK of the carboxylic acid lipid, the carboxylate groups are gradually neutralized and the PE-rich bilayer is destabilized.

PE lipids are prone to assume the inverted hexagonal phase ($H_{II}$) in the absence of stabilizing influences such as the presence of negatively charged head groups. In this instance, the hydrophobic region of the molecule is greater than that of the hydrophilic part of the molecule. Thus, lipids are released from liposome aggregates as the pH is lowered, resulting in extensive mixing with the endosomal membrane and improved cytoplasmic delivery of the liposome contents.

More recently, pH-sensitive cationic liposomes have been developed to mediate transfer of DNA into cells. For instance, researchers described a series of amphiphiles with headgroups containing imidazole, methylimidazole, or aminopyridine moieties (see, Budker et al., *Nature Biotech.*, 14, 760–764 (1996)). The amine-based headgroups possess pKs within the physiologic range of between 4.5 to 8. The hydrophobic domains for these lipids varied and included cholesterol and dioleoyl or dipalmitoyl glycerol. The pH sensitivity is a result of their titratable amine headgroups, a feature previously exploited that demonstrated pH-dependent fusion of liposomes containing poly-L-histidine (see, Uster et al., *Biochemistry*, 24, 1–8 (1985)). Acidification results in headgroup protonation and increases the effective headgroup size via electropositive repulsions. It has been postulated that the increased positive charge also increases the interactions with DNA and the anionic components of the endosomal membrane. These pH-dependent changes are believed to disrupt the liposome integrity, thus leading to fusion with the endosomal membrane and greater DNA escape. Thus, in the prior art methods, a decrease in pH causes assembly (e.g., liposome) reorganization.

In view of the foregoing, and in contrast to the known methods for reorganizing lipid assemblies as a function of pH, what is needed in the art are lipid molecules within the assemblies that are capable of structural reorganization upon a change in pH. Methods that use these lipids in liposome formulations in nucleic acid transfection are also needed. The present invention fulfills these as well as other needs.

SUMMARY OF THE INVENTION

In certain aspects, the present invention provides ortho ester lipids, and derivatives thereof, which upon certain pH conditions, undergo hydrolysis with concomitant or subsequent head group cleavage. As such, the present invention provides compounds of Formula I:

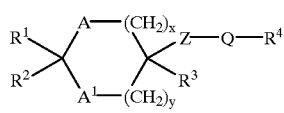

I

In Formula I, $R^1$ is a functional group including, but not limited to, optionally substituted ($C_7$–$C_{17}$)alkyl, optionally substituted ($C_7$–$C_{17}$)alkenyl and optionally substituted ($C_7$–$C_{17}$)alkynyl. $R^2$ is a functional group including, but not limited to, ($C_1$–$C_{18}$)alkoxy and ($C_1$–$C_{18}$)alkylthio. $R^3$ is a functional group including, but not limited to, hydrogen. In an alternative embodiment, $R^2$ and $R^3$ and the carbons to which they are bound, join to form a 5,6-membered; a 6,6-membered; a 6,7-membered; or a 7,7-membered bicyclic ortho ester or ortho thioester ring. A and $A^1$, which can be the same or different, are heteroatoms which include, but are not limited to, oxygen and sulfur. In Formula I, the index "x" is an integer having a value ranging from 0 to 2 inclusive. The index "y" is an integer having a value ranging from 0 to 2 inclusive. Z, in Formula I, is a functional group including, but not limited to, optionally substituted alkylene, optionally substituted alkyleneoxyalkylene and optionally substituted alkyleneaminoalkylene. In Formula I, Q is a functional group including, but not limited to, carboxyl, thiocarboxyl, dithiocarboxyl, phospho, phosphothio, phosphono and thiophosphono. In Formula I, $R^4$ is a nitrogen containing headgroup wherein the nitrogen can be unsubstituted, mono-substituted, di-substituted, or a quaternary nitrogen salt and wherein the nitrogen substituent(s) include, but are not limited to, optionally substituted ($C_1$-$C_{18}$)alkyl, optionally substituted ($C_2$-$C_{18}$)alkenyl, and optionally substituted ($C_2$-$C_{18}$)alkynyl and wherein $R^4$ and Q are optionally linked with a ($C_1$-$C_5$)alkylene or ($C_2$-$C_5$) alkenyl group.

DEFINITIONS

Figure 1A:
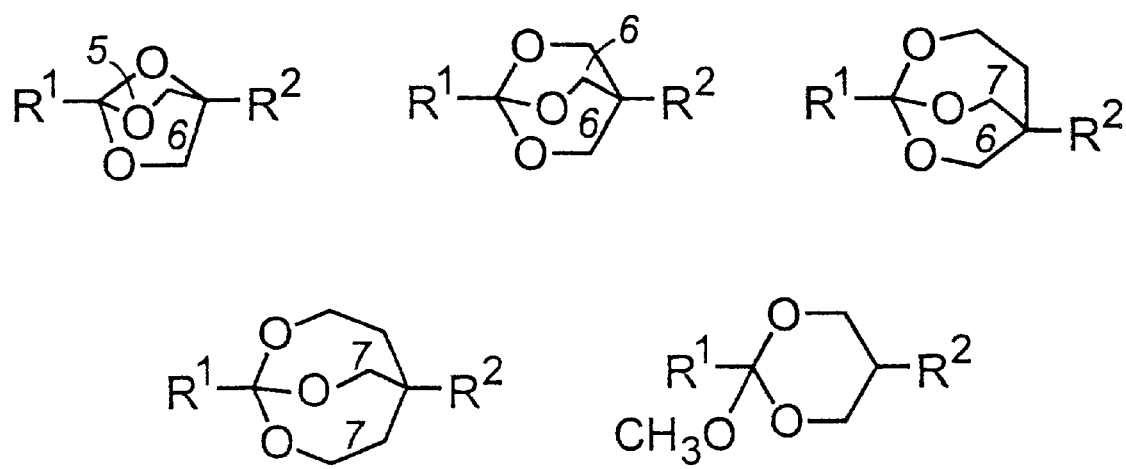
FIG. 1 (A–E) illustrates various functionalities of compounds of Formula I; (A) an ortho ester moiety, (B) a hydrophobic domain, (C) a linker, (D) a cleavable group and (E) a hydrophilic domain or head group.
Figure 1B:
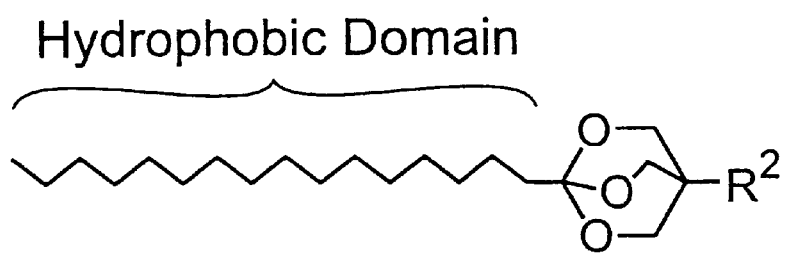
Figure 1C:
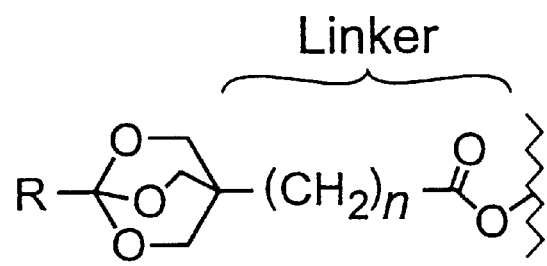
Figure 1D:
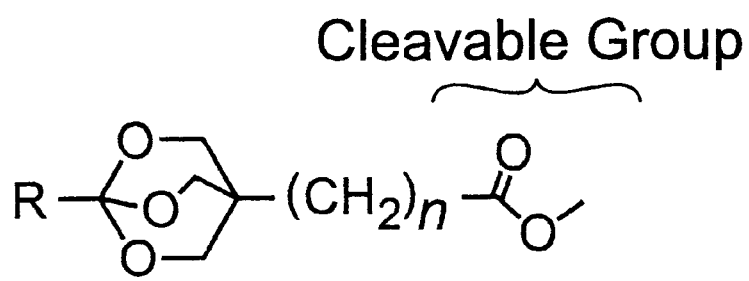
Figure 1E:
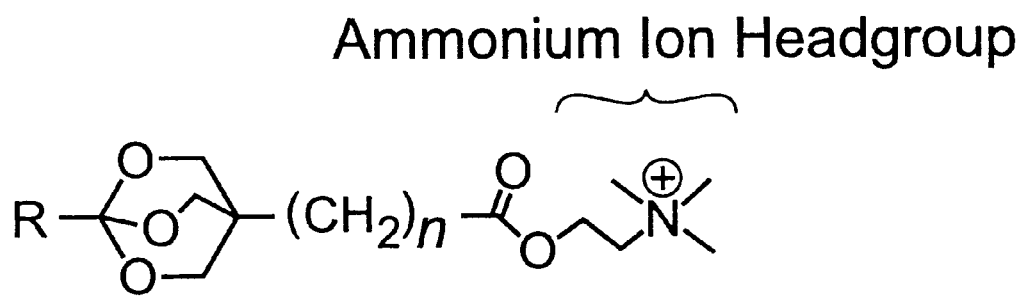

As used herein, the term "alkyl" denotes branched or unbranched hydrocarbon chains, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, alkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "alkylene" refers to a divalent alkyl as defined above, such as methylene (—$CH_2$—), propylene (—$CH_2CH_2CH_2$—), chloroethylene (—$CHClCH_2$—), 2-thiobutene —$CH_2CH(SH)CH_2CH_2$, 1-bromo-3-hydroxyl-4-methylpentene (—$CHBrCH_2CH(OH)CH(CH_3)CH_2$—), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aminoalkylene" denotes $H_2N$—$(CH_2$—$)_n$, wherein n is an integer.

The term "alkylaminoalkylene" denotes RNH—$(CH_2$—$)_n$, wherein n is an integer and R is an alkyl group as defined above.

The term "dialkylaminoalkylene" denotes RR'N—$(CH_2$—$)_n$, wherein n is an integer and R and R' are alkyl groups which may be the same are different as defined above.

The term "aryl" denotes a chain of carbon atoms which form at least one aromatic ring having preferably between about 6–14 carbon atoms, such as phenyl, naphthyl, indenyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like The term "acyl" denotes the —C(O)R group, wherein R is alkyl or aryl as defined above, such as formyl, acetyl, propionyl, or butyryl.

The term "acyloxyalkyl" denotes the R' C(O)OR— group, wherein R' R can be the same or different and are alkyl or aryl as defined above.

The term "alkoxy" denotes —OR—, wherein R is alkyl.

The term "amido" denotes an amide linkage: —C(O)NR— (wherein R is hydrogen or alkyl).

The term "amino" denotes an amine linkage: —NR—, wherein R is hydrogen or alkyl.

The term "carboxyl" denotes —C(O)O—, and the term "carbonyl" denotes —C(O)—.

The term "thiocarboxyl" denotes —C(S)O— or —C(O)S—

The term "dithiocarboxyl" denotes —C(S)S—

The term "carbonate" indicates —OC(O)O—.

The term "carbamate" denotes —NHC(O)O—.

The term "phospho" denotes —P(O)(OH)O—

The term "phosphothio" denotes —P(S)(OH)O— or —P(O)(OH)S—

The term "phosphoro" denotes —OP(O)(OH)O—.

The term "phosphorothio" denotes —OP(S)(OH)O— or —OP(O)(OH)S—.

The term "ortho ester" denotes a tetravalent carbon atom having three oxygen atoms and a carbon atom covalently attached thereto. One, two, or three sulfur atoms can substitute for the oxygens atoms to generate ortho thioesters.

The term "a nitrogen containing headgroup" denotes a nitrogen atom that can be unsubstituted (—$NH_2$), mono-substituted (—NHR) or di-substituted (—NRR') wherein R and R' can be the same or different and are independently selected from alkyl, alkenyl, or alkynyl as defined above.

The term "quaternary ammonium salt" denotes any one of the following structures: $H_3N$—$^+X^-$; $RNH_2$—$^+X^-$;

R$_2$NH—$^+$X$^-$; R$_3$N—$^+$X$^-$; wherein X is a counter ion, such as a halide ion, and wherein each R can be the same or different and each R is independently selected from alkyl, alkenyl, or alkynyl as defined above.

The term "optionally substituted" means that the functional group may or may not be substituted with one or more substituents listed above.

The term "5,6-membered; 6,6-membered; 6,7-membered; and 7,7-membered bicyclic ortho ester or ortho thioester ring" refers to a bridged bicyclo-system having 4 atoms common to both rings and having an ortho ester or ortho thioester moiety wherein each ring consists of 5, 6 or 7 atoms.

The term "fusion" refers to the ability of a liposome or other drug delivery system to fuse with membranes of a cell. The membranes can be either the plasma membrane or membranes surrounding organelles, e.g., endosome, nucleus, etc. "Fusogenesis" is the fusion of a liposome to such a membrane.

The term "cationic lipid" refers to any of a number of lipid species that carry a net positive charge at physiological pH. Such lipids include, but are not limited to, dimyristoyl bis(N,N,N-trimethylglycyl) tetraester ("DMTM(Gly)"); dioleoyl bis (N,N,N-trimethylglycyl) tetraester ("DOTM(Gly)"); N,N-dioleyl-N,N-dimethylammonium chloride ("DODAC"); N-(2,3-dioleoyloxy)propyl)-N,N,N-trimethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 3β-(N-(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y., USA); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate ("DOSPA") and ("DOPE"), from GIBCO/BRL); and TRANSFECTAM® (commercially available cationic lipids comprising dioctadecylamidoglycyl carboxyspermine ("DOGS") in ethanol from Promega Corp., Madison, Wis., USA). TFX® REAGENT (commercially available cationic liposomes comprising N,N,N',N'-tetramethyl-N,N'-bis(2-hydroxyethyl)-2,3-dioleoyloxy-1,4-butanediammonium iodide ("PolyGum") and ("DOPE"), from Promega Corp., Madison, Wis., USA.

The term "lipid aggregate" denotes liposomes both unilamellar and multilamellar as well as micelles and virosomes and more amorphous aggregates of cationic lipids or lipids mixed with amphipathic lipids such as phospholipids.

DETAILED DESCRIPTION OF THE INVENTION AND PREFERRED EMBODIMENTS

A. Compounds and Synthesis

In certain aspects, the present invention relates to ortho ester lipids and their derivatives that, upon certain pH conditions, undergo hydrolysis with concomitant or subsequent headgroup cleavage. Surprisingly, it has been discovered that by using an ortho ester functionality in amphipathic molecules, the compounds undergo acid-induced hydrolysis to their corresponding esters, and further fragmentation of the resultant ester into its constituent parts. Ortho ester conversion to its ester, with concomitant or subsequent head group cleavage, results in liposome disassembly. The pH-induced hydrolysis of the ortho ester moiety promotes liposome disassembly by altering either the lipid molecular structure (e.g., conversion of a dual-chain hydrophobic domain ortho ester lipid into a single-chain hydrophobic domain product) or by altering its amphiphilicity (e.g., loss of the polar head region). These processes, the liberation of single chain amphiphiles and/or head group cleavage, also effect destabilization of neighboring membranes. Thus, the compounds of the present invention have the ability to impart advantageous properties to liposomes by programming the liposomes to disassemble in response to certain pH conditions, and thereafter, destabilize or rupture encapsulating membranes (e.g., endosomal membrane).

As such, the present invention provides a compound of Formula I:

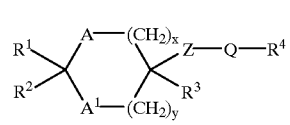

wherein R$^1$, R$^2$, R$^3$, A, A$^1$, x, y, Z, Q and R$^4$ have been previously defined. In general, the amphipathic compounds of Formula I can have a wide variety of variable functionalities and still remain within the scope of the current invention. The variable functionalities of compounds of Formula I include, but are not limited to, an ortho ester function, a hydrophobic domain, a linker, a cleavable group and a hydrophilic domain or nitrogen head group (see, FIG. 1).

Figure 2:
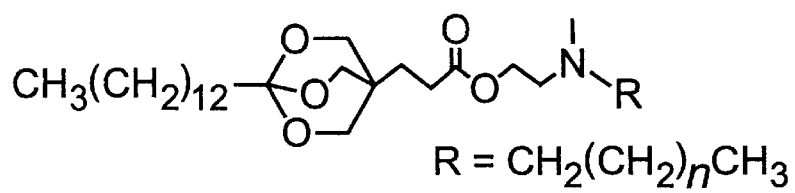
FIG. 2 illustrates a mechanism by which a compound of Formula I undergoes (i) hydrolysis and thereafter undergoes (ii) intramolecular transesterification to effect headgroup cleavage.
Figure 2:
Figure 2:
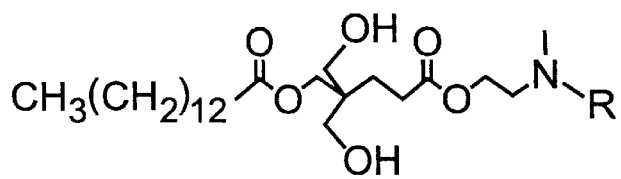
Figure 2:
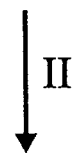
Figure 2:
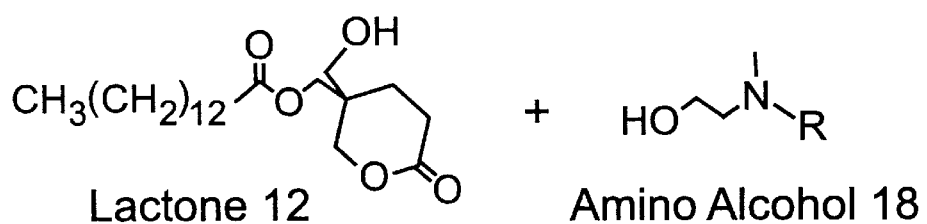

The compounds of Formula I comprise an ortho ester functionality or a derivative thereof. In general, ortho ester functionalities are among the most sensitive moieties toward acid-induced hydrolysis, more acid labile than for instance, acetals or enol-ethers. Without being bound by any particular theory, it is believed that compounds of Formula I undergo a 2 step decomposition process under acidic conditions. Using an illustrative embodiment, FIG. 2 shows a compound of the present invention undergoing acid induced hydrolysis. Step I illustrates ortho ester hydrolysis with generation of an ester functionality. Thereafter, the compounds of the present invention undergo further fragmentation in Step II via an intramolecular transesterification that results in headgroup cleavage. Decreasing pH facilitates both Step I and Step II. It is this unique 2-step or tandem mechanism which facilitates liposome disassembly when compounds of Formula I are incorporated into liposomes.

Although the ortho esters of the present invention are preferably bicyclic in nature, the compounds of Formula I are not limited as such. Again, upon a decrease in pH, the ortho esters of the present invention are (i) hydrolyzed and thereafter undergo (ii) intramolecular transesterification with concomitant or subsequent headgroup cleavage. In certain instances, such as when R$^2$ is an alkoxy group and R$^3$ is hydrogen, compounds of Formula I are not bicyclic. However, these compounds retain their 'self-cleaving' feature and ability to participate in the 2-step decomposition process discussed above.

In Formula I, A and A$^1$ can be the same or different heteroatom. By changing the nature of the heteroatoms making up the ortho ester functionality, (e.g., replacing an oxygen atom with a sulfur atom) the ortho esters become susceptible to hydrolysis at varying pH. Thus, it is possible to tailor or program the pH value where hydrolysis of the ortho ester (Step I, FIG. 2) will occur. Moreover, incorporation of sulfur enables oxidative means of ortho ester hydrolysis via sulfoxide or sulfone intermediates.

Figure 3:
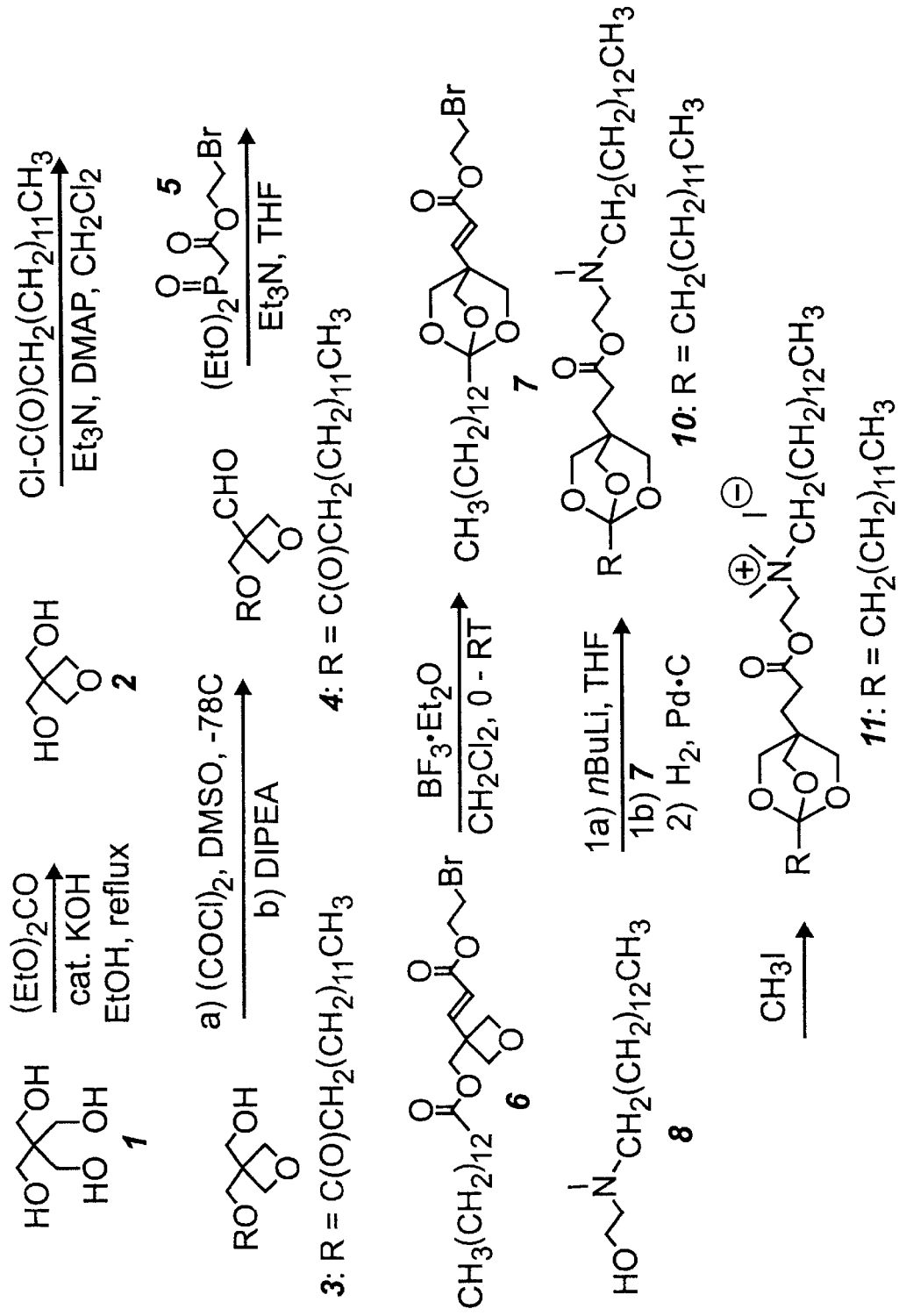
FIG. 3 illustrates a synthesis method to generate compounds of Formula I.
Figure 4:
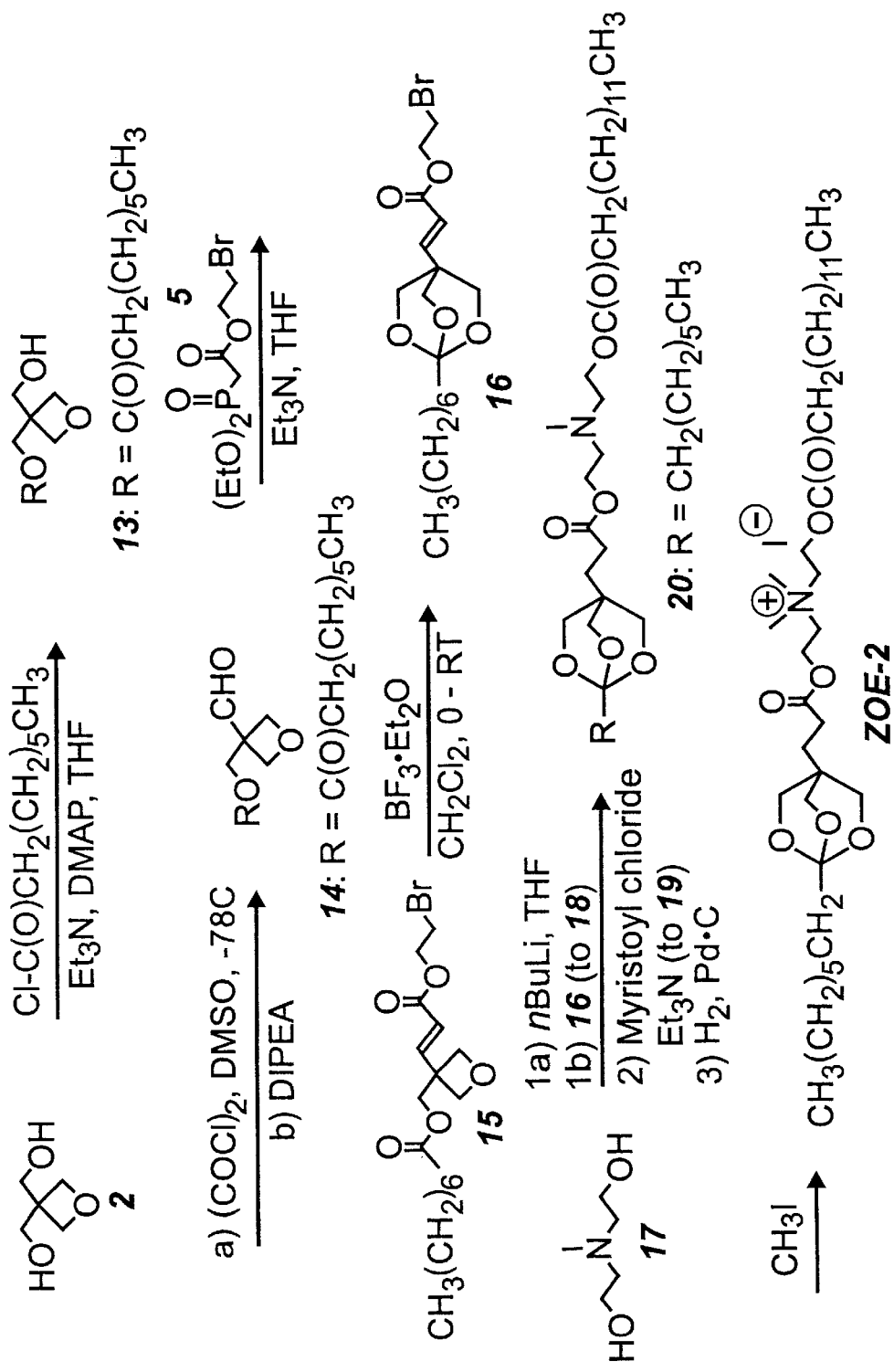
FIG. 4 illustrates a synthesis method to generate compounds of Formula I.

Compounds of Formula I can be prepared using various synthetic strategies. Two exemplary (representative) syntheses are shown in FIG. 3 and FIG. 4. With reference to FIG. 3, 3,3-bis(hydroxymethyl)oxetane 2 is generated from pentaerythritol 1 and diethyl carbonate in the presence of a base. Thereafter, (1-(hydroxymethyl)-3-oxetanyl)methyl tetradecanoate 3 is produced using oxetane 2 and myristoyl chloride.

In FIG. 3, myristoyl chloride is an example of a precursor to the hydrophobic domain portion of compounds of Formula I. The hydrophobic domain of Formula I can have a wide range of functionalities. Preferably, $R^1$ is a alkyl chain, which is optionally substituted. The alkyl chain can be a short chain or long chain. Representative functional groups include, but are not limited to, optionally substituted ($C_7$–$C_{17}$)alkyl, optionally substituted ($C_7$–$C_{17}$)alkenyl and optionally substituted ($C_7$–$C_{17}$)alkynyl. FIG. 4 illustrates a synthesis route that introduces a short alkyl chain for $R^1$, i.e., an octanoyl group.

Preferably, $R^1$ is optionally substituted ($C_{13}$–$C_{17}$)alkyl, optionally substituted ($C_{13}$–$C_{17}$)alkenyl and optionally substituted ($C_{13}$–$C_{17}$)alkynyl. In certain instances $R^1$ completes a myristyl group, an oleyl group, a lauryl group, a stearyl group or a palmityl group. Moreover, in certain embodiments, $R^1$ can be a dual chain hydrophobic group. A dual chain hydrophobic domain group can be incorporated into the molecule starting with, for example, an α-functionalized acid such as an α-hydroxy carboxylic acid or an α-acyloxy carboxylic acid, using an established synthesis routes as shown in FIG. 3 and FIG. 4. Representative carboxylic acids include, but are not limited to, myristic acid, oleic acid, laurylic acid, stearic acid and palmitic acid.

As shown in FIG. 3, (1-formyl-3-oxetanyl)methyl tetradecanoate 4 is generated from 3 using oxalyl chloride and DIPEA. This reaction allows for subsequent attachment of a linker group. In Formula I, a wide variety of linker groups (Z) can be used. In general, the linker unit connects a cleavable functionality such as a carboxyl group, to the ortho ester moiety. As shown in FIG. 2, ortho ester hydrolysis facilitates the intramolecular reaction between the hydrolysis product and the cleavable functionality. Suitable linking groups include, but are not limited to, optionally substituted alkylene, optionally substituted alkyleneoxyalkylene and optionally substituted alkyleneaminoalkylene. Preferably, the linker group is a one to three optionally substituted alkylene group(s), such as methylene, ethylene, or propylene. However, heteroatom substitution can be used to adjoin an ortho ester with the cleavable functionality (e.g., —$CH_2$—O—$CH_2CH_2$—).

The compounds of Formula I have a cleavable functionality adjacent to the linker group. Cleavable functional groups include, but are not limited to, carboxyl, thiocarboxyl, dithiocarboxyl, carbonate, carbamate, phospho, phosphothio, phosphoro and thiophosphoro. In certain embodiments, the preferred cleavable functionality is a carboxyl group. In other preferred embodiments, the phosphoro or thioester groups are used.

As illustrated in FIG. 3 and FIG. 4, the linker group and cleavable moiety can be incorporated into the ortho ester using the same reagent. In FIG. 3, 2-bromoethyl 3-(1-(tetradecanoyloxymethyl)-3-oxetanyl)prop-2-enoate 6 is generated from 4, using 2-bromoethyl diethylphosphonacetate 5. The ortho ester, 2-bromoethyl 3-(3,5,8-trioxa-4-tridecylbicyclo[2.2.2]octyl)prop-2-enoate 7, is generated from 6 with boron trifluoride etherate.

In certain embodiments, subsequent to ortho ester formation, a head group is attached. The head group preferably comprises a nitrogen atom, wherein the nitrogen can be unsubstituted, mono-substituted, di-substituted, or a quaternary nitrogen salt. The nitrogen substituent(s) which can be the same or different include, but are not limited to, optionally substituted ($C_1$–$C_{18}$)alkyl, optionally substituted ($C_2$–$C_{18}$)alkenyl, and optionally substituted ($C_2$–$C_{18}$)alkynyl. $R^4$ and Q are optionally linked with an alkylene or alkenyl group.

In preferred embodiments, the ortho ester functionality comprises a bicyclic ring system wherein $R^2$ and $R^3$ and the carbons to which they are bound, join to form a 5,6-membered; a 6,6-membered; a 6,7-membered; or a 7,7-membered bicyclic ortho ester or ortho thioester ring. In an especially preferred embodiment, the compounds of Formula I form a 6,6-membered bicyclic ortho ester ring having Formula II:

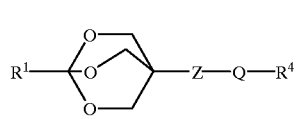

wherein $R^1$, Z, Q and $R^4$ have been defined previously.

In Formula II certain substituents are preferred. For example, $R^1$ is preferably ($C_7$–$C_{17}$)alkyl optionally substituted with ($C_7$–$C_{18}$)acyloxy, and $R^1$ is more preferably, ($C_{13}$–$C_{17}$)alkyl (e.g., $C_{13}$) and ($C_{14}$)acyloxy($C_{13}$)alkyl. Z is preferably optionally substituted alkylene, and more preferably, ($C_1$–$C_3$)alkylene. Q is preferably a carboxyl group.

$R^4$ is preferably optionally substituted amino($C_1$–$C_5$)alkylene, optionally substituted ($C_1$–$C_{18}$)alkylamino($C_1$–$C_5$)alkylene, optionally substituted ($C_1$–$C_{18}$)alkyl amino($C_2$–$C_5$)alkenyl, optionally substituted ($C_1$–$C_{18}$)dialkylamino($C_1$–$C_5$)alkylene, optionally substituted ($C_1$–$C_{18}$)dialkylamino($C_2$–$C_5$)alkenyl or an ammonium salt of any of the foregoing.

$R^4$ is more preferably ($C_1$–$C_{18}$)dialkylamino($C_1$–$C_3$)alkylene, such as N-methyl-N-tetradecanyl amino($C_2$)alkylene or an ammonium salt thereof such as N,N-dimethyl-N-tetradecanylamino($C_2$)alkylene; ($C_1$–$C_{18}$)acyloxyalkyleneamino($C_1$–$C_3$)alkylene, such as ($C_{15}$)acyloxy($C_2$)alkyleneamino($C_2$)alkylene or an ammonium salt thereof such as N,N-dimethyl-($C_{15}$)acyloxy($C_2$)alkyleneamino($C_2$)alkylene.

In certain preferred embodiments, $R^4$ is a quaternary ammonium salt having the structure $R^5R^6R^7N^+$—$(CH_2)_n$—$X^-$ wherein $R^5$, $R^6$ and $R^7$ are members independently selected from the group of hydrogen, optionally substituted ($C_2$–$C_{18}$)alkyl, optionally substituted ($C_1$–$C_{18}$)alkenyl and optionally substituted ($C_2$–$C_{18}$)alkynyl; X is a counter ion, such as a halide ion, and n is an integer between 0 and 5 inclusive. In one embodiment, $R^5$ and $R^6$ are both short chain alkanes, such as two methyl groups, and $R^7$ is a long hydrocarbon chain (e.g., ($C_7$–$C_{17}$)alkyl) that is optionally substituted, unsaturated, or both. Suitable counter ions include, but are not limited to, chloride, iodide, fluoride and bromide. Iodide is the preferred counter ion.

Figure 6:
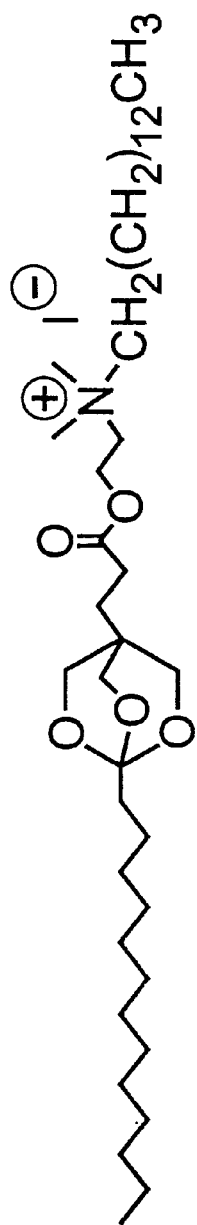
FIG. 6 illustrates examples of compounds of Formula I.
Figure 6:
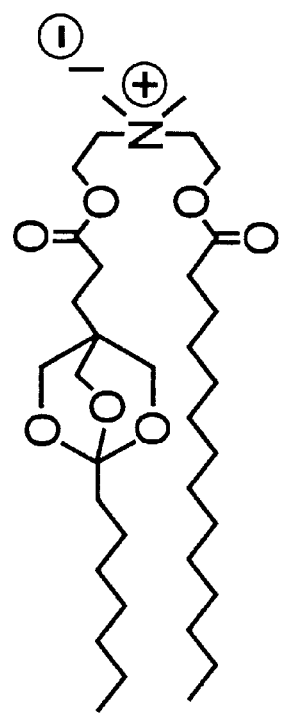

Compounds of Formula I that are especially preferred are N,N-dimethyl-N-tetradecyl-N-(2-[3-(3,5,8-trioxa-4-tridecylbicyclo[2.2.2]octyl)propanoyloxy]ethyl) ammonium iodide (ZOE-1) and N,N-dimethyl-N-(2-[3-(3,5,8-trioxa-4- heptylbicyclo-[2.2.2]octyl)propanoyl-oxy]ethyl)-N-(2-tetradecanoyloxy)ethyl ammonium iodide (ZOE-2) (see, FIG. 6).

The compounds of Formula I exploit the susceptibility of the ortho ester functional group toward acid induced hydrolysis. Moreover, the putative mechanism of action for the ortho ester lipids of the present invention involves structural reorganization of the lipids beyond their protonation. Acidification of ortho ester lipids results in lipid (and liposome) structural changes i.e., ortho ester conversion to an ester with headgroup cleavage and liposome disassembly. Thus, the compounds of the present invention are advantageously incorporated into liposome formulations as described hereinbelow.

B. Liposome Preparation and Composition

In another aspect, the present invention relates to a lipid formulation comprising a compound of Formula I and a bioactive agent. In certain aspects, the bioactive agent is a nucleic acid. In other aspects, the lipid formulation is a lipid-nucleic acid complex comprising a nucleic acid and at least one compound of Formula I. The lipid formulation is preferably a liposome formulation. In another preferred aspect, the bioactive agent is an organic or inorganic small molecule drug.

The compounds of Formula I can be used alone, or in combination with a "helper" lipid. Preferred helper lipids are non-ionic or uncharged at physiological pH. Particularly preferred non-ionic lipids include, but are not limited to, cholesterol and DOPE, with cholesterol being most preferred. The molar ratio of a compound of Formula I to helper can range from 3:1 to about 1:3, more preferably from about 1.5:1 to about 1:1.5 and most preferably is about 1:1.

Liposomes of the present invention are constructed by well-known techniques, such as described in *Liposome Technology*, Vols. 1–3 (G. Gregoriadis, Ed., CRC Press, 1993). Lipids are typically dissolved in chloroform and spread in a thin film over the surface of a tube or flask by rotary evaporation. If liposomes comprised of a mixture of lipids is desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires some minutes depending upon conditions, kind, and quality of the sonicator. Commonly, lipid concentrations are 1 mg/mL of aqueous phase, but could easily be higher or lower by a factor of ten.

The liposomes of the present invention comprise one or more of the compounds of Formula I. Liposomes according to the invention optionally have one or more other amphiphiles. The exact composition of the liposomes will depend on the particular circumstances for which they are to be used. Those of ordinary skill in the art will find it a routine matter to determine a suitable composition. The liposomes of the present invention comprise at least one compound of the present invention. In a preferred embodiment, the liposomes of the present invention consist essentially of a single type of lipid of Formula I. In another preferred embodiment, the liposomes comprise mixtures of compounds of Formula I. In yet another preferred embodiment, the liposomes of the present invention comprise one or more lipids of Formula I in a mixture with one or more natural or synthetic lipids, e.g., cholesterol or DOPE.

In a preferred embodiment, mostly unilamellar liposomes are produced by the reverse phase evaporation method of Szoka & Papahadjopoulos, *Proc. Natl. Acad. Sci.* USA, 75: 4194–4198 (1978). Unilamellar vesicles are generally prepared by sonication or extrusion. Sonication is generally performed with a bath-type sonifier, such as a Branson tip sonifier at a controlled temperature as determined by the melting point of the lipid. Extrusion may be carried out by biomembrane extruders, such as the Lipex Biomembrane Extruder. Defined pore size in the extrusion filters may generate unilamellar liposomal vesicles of specific sizes. The liposomes can also be formed by extrusion through an asymmetric ceramic filter, such as a Ceraflow Microfilter, commercially available from the Norton Company, Worcester Mass.

Following liposome preparation, the liposomes that have not been sized during formation may be sized by extrusion to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Several techniques are available for sizing liposomes to a desired size. One sizing method is described in U.S. Pat. Nos. 4,529,561 or 4,737,323, herein incorporated by reference. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10: 421–450 (1981). Average liposome diameter may be reduced by sonication of formed liposomes. Intermittent sonication cycles may be alternated with QELS assessment to guide efficient liposome synthesis.

Extrusion of liposomes through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve a gradual reduction in liposome size. For use in the present invention, liposomes having a size of about 0.05 microns to about 0.5 microns. More preferred, are liposomes having a size of about 0.05 to 0.2 microns.

C. Nucleic Acid

Nucleic acids of all types may be associated with the compounds of Formula I and liposomes of the present invention and subsequently can be transfected. These include DNA, RNA, DNA/RNA hybrids (each of which may be single or double stranded), including oligonucleotides such as antisense oligonucleotides, chimeric DNA-RNA polymers, and ribozymes, as well as modified versions of these nucleic acids wherein the modification may be in the base, the sugar moiety, the phosphate linkage, or in any combination thereof.

From the foregoing it will be clear to those skilled in the art that the liposomes of the present invention are useful for both in vitro and in vivo application. The liposomes of the present invention will find use for nearly any in vitro application requiring transfection of nucleic acids into cells. For example, the process of recombinant production of a protein.

The nucleic acids may comprise an essential gene or fragment thereof, in which the target cell or cells is deficient in some manner. This can occur where the gene is lacking or where the gene is mutated resulting in under- or over-expression. The nucleic acids can also comprise antisense oligonucleotides. Such antisense oligonucleotides may be constructed to inhibit expression of a target gene. The foregoing are examples of nucleic acids that may be used with the present invention, and should not be construed to limit the invention in any way. Those skilled in the art will appreciate that other nucleic acids will be suitable for use in the present invention as well.

D. Conventional Drugs

The liposome formulations and methods of the present invention can be used to deliver a broad range of conventional pharmaceuticals and therapeutic drugs. In addition to the aforementioned nucleic acids, in certain aspects, the liposome formulations of the present invention comprise small organic or inorganic compounds as bioactive agents. As is illustrated in Example 4, in certain embodiments, the liposomal formulations of the present invention can encapsulate a bioactive agent and then release the encapsulated contents upon mild acidic conditions. In Example 4, encapsulated calcein was released upon lowering the pH. Thus, the liposomal formulations comprising a pH-sensitive compound of Formula I can advantageously be used to entrap, release and deliver therapeutic agents.

Suitable conventional pharmaceuticals or bioactive agents include, but are not limited to, antimicrobials, antibiotics, antimyobacterial, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, antiarthritics, and diagnostic agents.

In certain preferred aspects, the bioactive agent will be an antineoplastic agent, such as vincristine, doxorubicin, mitoxantrone, camptothecin, cisplatin, bleomycin, cyclophosphamide, methotrexate, streptozotocin, and the like. Especially preferred antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs.

In certain aspects, the liposome formulations of the present invention are used to deliver anti-infective agents. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; anti-depressants, e.g., imipramine, amitriptyline and doxepim; anti-conversants, e.g., phenytoin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents. Those of skill in the art will know of other agents suitable for use with the formulations and methods of the present invention.

E. Method for Transfecting

In yet another aspect, this invention relates to a method for transfecting a nucleic acid into a cell. The method involves contacting a cell with a lipid-nucleic acid complex or aggregate comprising a nucleic acid and an amphiphilic compound of Formula I. Liposome-nucleic acid complex/aggregates may be prepared by adding an appropriate amount of nucleic acid to a liposome solution. For transfection, the weight ratio of compound of Formula I to DNA is from slightly over 1:1 to perhaps 10:1. The amount of DNA can vary considerably, but is normally a few to a few tens of micrograms per standard culture dish of cells. Conditions can vary widely, and it is a routine matter and standard practice to optimize conditions for each type of cell, as suppliers of commercial materials recommend. Optimization involves varying the lipid to DNA ratio as well as the total amount of aggregate.

There is currently some uncertainty regarding the precise way in which nucleic acids and compound of Formula I interact. In addition, the structure formed both before and during the transfection process is not definitively known. The present invention, however, is not limited by the particular structural type of complex formed by the liposomes and lipid aggregates of the present invention and the nucleic acids to be transfected. The phrase "liposome-nucleic acid aggregate" means any association of liposome or compound of Formula I and nucleic acid that is capable of lipofection.

The lipid-nucleic acid aggregate is added to the cells, in culture medium, and left for some tens of minutes to several hours to perhaps overnight. Usually serum is omitted from the culture medium during this phase of transfection. Subsequently, the medium is replaced with normal, serum-containing medium and the cells are incubated for hours to days or possibly cultured indefinitely.

Figure 8:
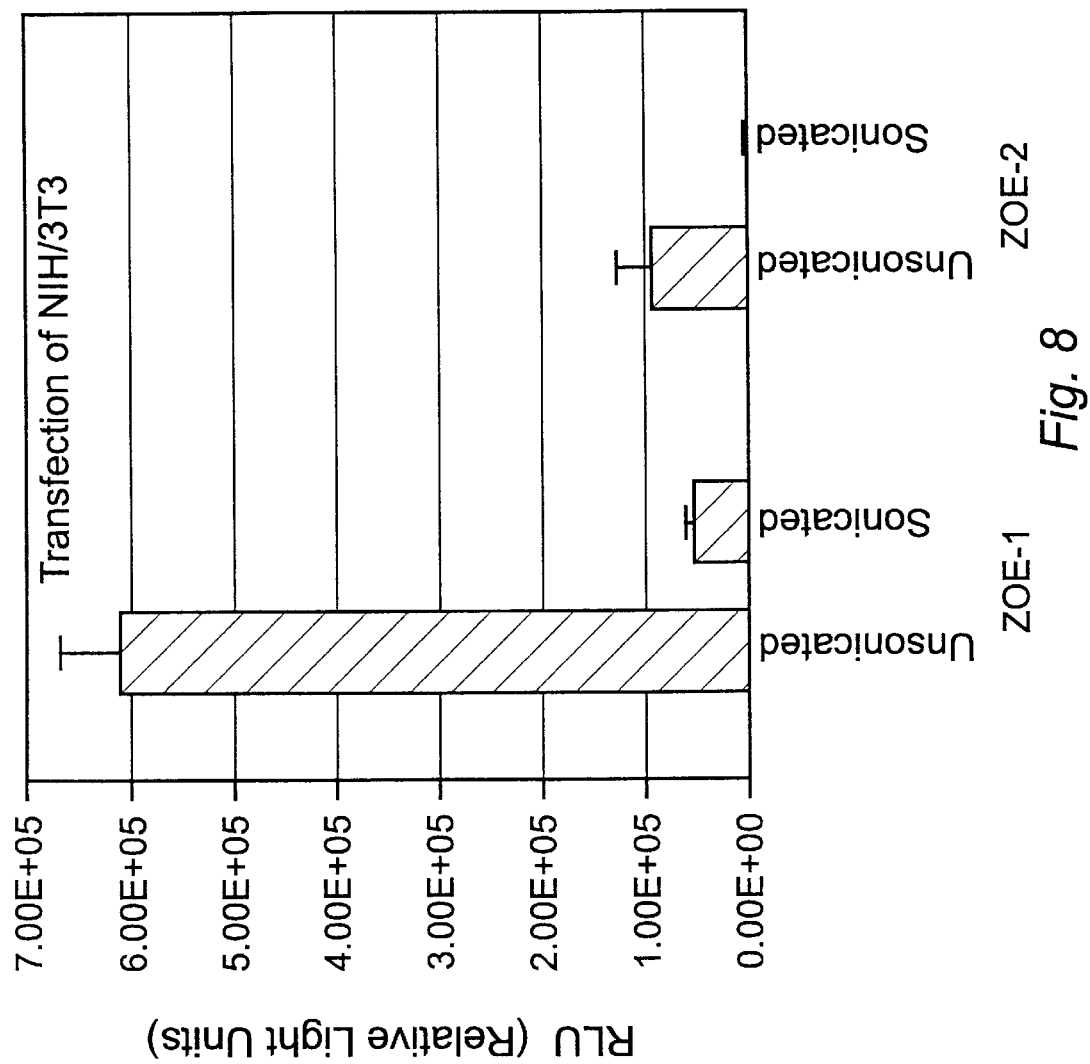
FIG. 8 illustrates relative luciferase activity using compounds and methods of the present invention.

With reference to FIG. 8, results of transfection experiments using compounds of the present invention are shown. As illustrated therein, compounds of Formula I are successful in delivering plasmid DNA into cells.

F. Specific Target Tissues

Specific targeting moieties can be used with the lipid-:nucleic acid complexes of this invention to target specific cells or tissues. In one embodiment, the targeting moiety, such as an antibody or antibody fragment, is attached to a hydrophilic polymer and is combined with the lipid:nucleic acid complex after complex formation. Thus, the use of a targeting moiety in combination with a generic effector lipid:nucleic acid complex provides the ability to conveniently customize the novel pH sensitive complex for delivery to specific cells and tissues.

Examples of effectors in lipid:nucleic acid complexes include nucleic acids encoding cytotoxins (e.g., diphtheria toxin (DT), Pseudomonas exotoxin A (PE), pertussis toxin (PT), and the pertussis adenylate cyclase (CYA)), antisense nucleic acid, ribozymes, labeled nucleic acids, and nucleic acids encoding tumor suppressor genes such as p53, p110Rb, and p72. These effectors can be specifically targeted to cells such as cancer cells, immune cells (e.g., B and T cells), and other desired cellular targets with a targeting moiety. For example, as described above, many cancers are characterized by overexpression of cell surface markers such as HER2, which is expressed in breast cancer cells, or IL17R, which is expressed in gliomas. Targeting moieties such as anti-HER2 and anti-IL17R antibodies or antibody fragments are used to deliver the lipid:nucleic acid complex to the cell of choice. The effector molecule is thus delivered to the specific cell type, providing a useful and specific therapeutic treatment.

G. Drug Delivery

In still yet another aspect, this invention relates to a pharmaceutical composition or other drug delivery composition for administering a nucleic acid particle to a cell. This composition includes a lipid-nucleic acid complex comprising a nucleic acid and a compound of Formula I, and a pharmaceutically acceptable carrier therefor. As used herein, the term "pharmaceutical composition" means any association of a liposome or compound of Formula I and a nucleic acid and or a mixture of a conventional drug capable of being delivered into cells.

Cationic lipid-assisted drug delivery can be accomplished in the following manner. For drugs that are soluble in organic solvents, such as chloroform, the drug and cationic lipid are mixed in solvents in which both are soluble, and the solvent is then removed under vacuum. The lipid-drug residue is then dispersed in an appropriate aqueous solvent, which, in a preferred embodiment, is sterile physiological saline. The suspension then may optionally be subjected to up to several freeze/thaw cycles. It is then sonicated, either merely to reduce the coarseness of the dispersion or to reduce the particle size to 20–30 nm diameter, depending upon whether large or small particle size is most efficacious in the desired application. For some applications, it may be most effective to generate extruded liposomes by forming the suspension through a filter with pores of 100 nm diameter or smaller. For some applications, inclusion of cholesterol or natural phospholipids in the mixture used to generate the lipid-drug aggregate can be appropriate.

The pH sensitive ortho ester liposome formulations of the present invention that comprise a bioactive agent can be delivered in any suitable manner. For drugs that are soluble in aqueous solution and insoluble in organic solvents, the lipid mixture to be used for the lipid dispersion or liposomes is coated on the inside surface of a flask or tube by evaporating the solvent from a solution of the mixture. In general, for this method to be successful, the lipid mixture must be capable of forming vesicles having single or multiple lipid bilayer walls and encapsulating an aqueous core. The aqueous phase containing the dissolved drug, preferably a physiological saline solution, is added to the lipid, agitated to generate a suspension, and then optionally frozen and thawed up to several times.

To generate small liposomes the suspension is subjected to ultrasonic waves for a time necessary to reduce the liposomes to the desired average size. If large liposomes are desired, the suspension is merely agitated by hand or on a vortex mixer until a uniform dispersion is obtained, i.e., until visually observable large particles are absent. If the preparation is to have the drug contained only within the liposomes, then the drug in the aqueous phase is eliminated by dialysis or by passage through a gel-filtration chromatographic column (e.g., agarose) equilibrated with the aqueous phase containing all normal components except the drug. The lipid mixture used can contain cholesterol or natural lipids in addition to the cationic compounds of the present invention. The liposome-drug aggregate may then be delivered in any suitable manner. In certain aspects, the liposomal formulations of the present invention improve drug delivery because of their sensitivity to pH, endosomal escape is promoted.

H. Disease Treatment

In yet another aspect of the invention comprises novel methods of treating diseases arising from infection by a pathogen or from an endogenous DNA deficiency. These methods comprise administering a liposome-nucleic acid aggregate and/or liposome-drug aggregate solution to a mammal suffering from a pathogenic infection or DNA deficiency. If the disease is the result of infection by a pathogen, the nucleic acid can be an antisense oligonucleotide targeted against an DNA sequence in the pathogen that is essential for development, metabolism, or reproduction of the pathogen. If the disease is a DNA deficiency (i.e., wherein certain endogenous DNA is missing or has been mutated), resulting in under- or over-expression, the nucleic acid maybe the normal DNA sequence.

Several methods of in vivo lipofection have been reported. In the case of whole animals, the lipid-nucleic acid aggregate may be injected into the blood stream, directly into a tissue, into the peritoneum, instilled into the trachea, or converted to an aerosol, which the animal breathes. Zhu, et al., *Science* 261, 209–211 (1993) describe a single intravenous injection of 100 micrograms of a mixture of DNA and DOTMA:dioleoylphosphatidylethanaolamine that efficiently transfected virtually all tissues. It is also possible to use a catheter to implant liposome-DNA aggregates in a blood vessel wall, which can result in successful transformation of several cell types, including endothelial and vascular smooth muscle cells. Stribling, et al., *Proc. Natl. Acad. Sci. USA* 89, 11277–11281 (1992), demonstrated that aerosol delivery of a chloramphenicol acetyltransferase (CAT) expression plasmid complexed to cationic liposomes produced high-level, lung-specific CAT gene expression in mice in vivo for at least 21 days. They described the following procedure: Six milligrams of plasmid DNA and 12 $\mu$mol of DOTMA/DOPE liposomes were each diluted to 8 mL with water and mixed; equal volumes were then placed into two Acorn I nebulizers (Marquest, Englewood, Colo.); animals were loaded into an Intox small-animal exposure chamber (Albuquerque) and an air flow rate of 4L/ min was used to generate the aerosol (about 90 min were required to aerosolize this volume) the animals were removed from the chamber for 1–2 hours and the procedure was repeated. This protocol is representative of the aerosol delivery method.

The Examples set forth below reflect opportunities for introduction of the diverse structural features described by Formula I. However, they are presented for illustrative purposes only and are not intended, and should not be construed, to limit the invention in any manner.

EXAMPLES

Methods $^1$H and $^{13}$C spectra were recorded at 300 and 75 MHz respectively, using $CDCl_3$ (unless noted otherwise) as solvent. Chemical shifts are given in units with respect to residual $CHCl_3$ (7.26 ppm for $^1$H) or $CDCl_3$ (77.0 ppm center line in $^{13}$C). Infrared (IR) spectra were obtained on a Mattson FTIR 3000 infrared spectrophotometer using solutions in $CHCl_3$ unless otherwise noted. Melting points are uncorrected. High-resolution mass spectra determinations were conducted at the University of Minnesota, Mass spectrum facility (Minneapolis, Minn.) and University of Colorado at Boulder, Center Analytical Laboratory (Boulder, Colo.). Elemental analyses were performed by Midwest Mirolabs of Indianapolis, Ind. Column chromatography was carried out on 230–400 mesh silica gel, slurry packed in glass columns, eluting with the solvents indicated. Thin layer chromatography was performed on Merck Kieselgel 60 F254 plates, staining with an ethanolic phosphomolybdic acid and sulfuric acid solution.

Example 1

This Example illustrates the synthesis of 2-(Methyltetradecylamino)ethyl 3-(3,5,8-trioxa-4-tridecylbicyclo[2.2.2]octyl) propanoate (10) (see, FIG. 3).

A. 3,3-Bis(hydroxymethyl)oxetane 2.

A 100 mL round bottom flask was charged with diethyl carbonate (27.7 mL, 228 mmol), pentaerythritol (25 g, 179 mmol), potassium hydroxide (50 mg) and 3 mL anhydrous ethanol. The reaction mixture was heated at 135° C. After 4 hours, an additional portion of potassium hydroxide (50 mg) was added to the reaction and the ethanol was removed by distillation over 3 h. The reaction was then heated gradually to 170° C. over 1 h. The turbid solution was then heated to 190° C. for ca. 1 to 1.5 h until the solution cleared. The product was isolated from the reaction mixture by distillation under vacuum (0.5 mm Hg) at 180–190° C. (lit. bp=123° C., 0.35 mm Hg). In this manner, 10 g (45%) was obtained as a semi-solid. $^1$H NMR (d$_6$-DMSO) δ 3.54 (d, J=5 Hz, 4H), 4.26 (s, 4H), 4.70(t, J=5 Hz, 2H).

B. (1-Hydroxymethyl)-3-oxetanyl)methyl tetradecanoate 3.

Oxetane 2 (5 g, 41 mmol) was dried in vacuo at 100° C. for 1 h and then dissolved in THF (120 mL). To the solution at room temperature was added freshly distilled triethylamine (10 mL, 72 mmol) and N,N-(dimethylamino)pyridine (400 mg, 3.3 mmol) and the reaction was cooled to 0° C. Myristoyl chloride (8.9 mL, 33 mmol) was added via cannula to the reaction mixture, and the resulting yellowish solution was stirred at 0° C. for 4 h and then warmed to room temperature and stirred an additional 4 h. The reaction was quenched by addition of diethyl ether and washing with sat'd aq. NaHCO$_3$, followed by washing with brine. The organic layer was separated and dried (Na$_2$SO$_4$). The solvents were removed by rotary evaporation, and the crude product was purified by silica gel column chromatography to yield 8 g (74%) of the ester 3 as white powder.

mp=49.5–50.5° C.; TLC (1:1, HOAc:Hex) R$_f$=0.25. IR (CHCl$_3$) 3371, 2914, 2850, 1736 cm$^{-1}$. $^1$H NMR (CDCl$_3$) δ 4.51 (m, 4H), 4.45 (s, 2H), 3.83 (d, J=5.7 Hz, 2H), 2.38 (t, J=7.6 Hz, 2H), 2.20 (t, J=5.7 Hz, 1H), 1.65 (m, 2H), 1.35 (m, 20H), 0.88 (t, J=6.3 Hz, 3H). $^{13}$C NMR δ 174.4, 75.9, 64.9, 64.1, 44.2, 34.2, 31.9, 29.6 (m), 25.0, 22.7, 14.1.

C. (1-Formyl-3-oxetanyl)methyl tetradecanoate 4.

To a solution of oxalyl chloride (1.3 mL, 14.6 mmol) in CH$_2$Cl$_2$ (25 mL) at −78° C. was added dropwise dry DMSO (2.3 mL, 30 mmol). The resulting mixture was stirred at −78° C. for 15 minutes whereupon a solution of ester 3 (3 g, 9.2 mmol) in CH$_2$Cl$_2$ (20 mL) was added to slowly via cannula. After stirring at −78° C. for 1.5 hours, dry DIPEA (8 mL, 46 mmol) was add via syringe and the reaction was stirred at −78° C. an additional 30 mins. before warming to 0° C. and stirring for 10 mins. The reaction was diluted with CH$_2$Cl$_2$ and washed with 3% ammonium chloride (3×200 mL). The organic layer was separated dried (Na$_2$SO$_4$). After removal of the solvents, the crude solid was purified by silica gel column chromatography, eluting with a gradient of 25 to 50% ethyl acetate in hexane, to afford 2.4 g (80%) of aldehyde 4 as white solid.

mp=40.2–41.8° C.; TLC (1:1, HOAc:Hex) R$_f$=0.40; IR (CHCl$_3$) 2925, 2854, 1720, 1465 cm$^{-1}$; $^1$H NMR (CDCl$_3$) δ 9.95 (s, 1H), 4.88 (d, J=4.5 Hz, 2H), 4.56 (d, J=7.8 Hz, 4H), 2.25 (t, J=7.8 Hz, 2H), 1.65 (m, 2H), 1.30 (m, 20H), 0.85 (m, 3H). $^{13}$C NMR (CDCl$_3$) δ 198.1, 173.5, 72.7, 63.1, 52.4, 34.0, 31.1, 29.6(m), 24.8, 22.7, 14.1.

D. 2-Bromoethyl 3-(1-(tetradecanoyloxymethyl)-3-oxetanyl)prop-2-enoate 6.

To a solution of aldehyde 4 (2.0 g, 6.1 mmol) in THF (50 mL) at 0° C. was added triethylamine (8.5 mL, 61 mmol) and lithium bromide (2.4 g, 24.5 mmol). To the reaction mixture was then added a solution of the phosphonate reagent (1.86 g, 6.13 mmol) in THF (20 mL) via cannula. The mixture was stirred at 0° C. for 0.5 h and then warmed to room temperature and stirred an additional 4 h. The reaction was diluted with diethyl ether and washed with brine, and the resulting organic layer was separated and dried (Na$_2$SO$_4$). The solvents were removed by rotary evaporation and the residue was purified by column chromatography, eluting with 20% ethyl acetate in hexane containing 1% triethyl amine, to obtain 2.30 g (79%) of the vinyl ester 6 as a colorless oil. TLC (35:65, HOAc:Hex) R$_f$=0.60 IR (CHCl$_3$) 2924, 2854, 1734, 1654, 1467 cm$^{-1}$ $^1$H NMR (CDCl$_3$) δ 7.15 (d, J=16.1 Hz, 1H), 6.00 (d, J=16.2 Hz, 1H), 4.66–4.56 (m, 4H), 4.53(t, J=6.1 Hz, 2H), 4.40(s, 2H), 3.54(t, J=6.1 Hz, 2H), 2.32(t, J=7.4 Hz, 2H), 1.58 (m, 2H), 1.24 (m, 20H), 0.88 (t, J=6.7 Hz, 3H); $^{13}$C NMR (CDCl$_3$) δ 173.1, 164.9, 147.3, 121.0, 66.3, 63.6, 44.1, 33.6, 31.4, 29.1(m), 28.0, 24.4, 22.2, 13.6 HRMS calcd for C$_{23}$H$_{39}$O$_5$Br, 475.2059; Found 475.2064.

E. Preparation of 2-Bromoethyl Diethylphosphonacetate 5

To a solution of diethyl-phosphonacetic acid (3 mL, 18.3 mmol) in CH$_2$Cl$_2$ (50 mL) at 0° C. was added DCC (5.62 g, 27.5 mmol) in one portion. 2-Bromoethanol (2.0 mL, 27.6 mmol) and N,N-(dimethylamino)pyridine (100 mg, 0.82 mmol) were added to the resultant white suspension and the suspension was stirred at room temperature 36 h. The suspension was filtered and the retentate was washed with diethyl ether. The filtrate was then triturated with diethyl ether several times to precipitate remaining DCU that was removed by filtration. The solvents were removed by rotary evaporation and the residue was purified by column chromatography, eluting with 2% MeOH in CH$_2$Cl$_2$, to obtain the HWE reagent as colorless liquid containing residual DCU. $^1$H NMR (CDCl$_3$) δ 4.43 (t, J=6.0 Hz, 2H), 4.13 (q, J=7.3 Hz, 4H), 3.50 (t, J=6.0 Hz, 2H), 3.00 (d, J=10.5 Hz, 2H), 1.36 (t, J=7.3 Hz, 6H); $^{13}$C NMR (CDCl$_3$) δ 164.9, 64.3, 62.4, 62.3, 34.6, 32.8, 27.6, 15.9.

F. 2-Bromoethyl 3-(3,5,8-trioxa-4-tridecylbicyclo[2.2.2]octyl)prop-2-enoate 7.

To a solution of the vinyl ester 6 (2.3 g, 4.8 mmol) in CH$_2$Cl$_2$ (50 mL) at 0° C. was added boron trifluoride etherate (92 μL, 7.2 mmol). The reaction solution was gradually warmed to room temperature and stirred 12h. The reaction was cooled to 0° C. and quenched by addition of triethylamine (0.67 mL, 4.82 mmol) and stirred 0.5 h. The mixture was diluted with Et$_2$O and filtered through a pad of Celite to remove the boron trifluoride·triethylamine complex. The filtrate was concentrated by rotary evaporation to yield the crude product which was purified by column chromatography (NOTE: the SiO$_2$ must be pretreated by storing as a slurry in hexane containing 1% triethylamine), eluting with a gradient of 25%–50% ethyl acetate in a hexane solution containing 1% triethylamine, to obtain 1.55 g (67.4%) of ortho ester 7 as white solid.

mp=58.5–61° C.; TLC (35:65, HOAc:Hex) R$_f$=0.60 IR (CHCl$_3$) 2921, 2850, 1718, 1654,1469 cm$^{-1}$; $^1$H NMR (CDCl$_3$) δ 6.63 (d, J=16.3 Hz, 1H), 5.77 (d, J=16.2 Hz, 1H), 4.45 (t, J=6 Hz, 2H), 4.06 (s, 6 Hz), 3.53 (t, J=6 Hz, 2H), 1.66 (t, J=4.7 Hz, 2H), 1.44–1.40 (m, 2H), 1.24 (m, 20 Hz), 0.88 (t, J=6.1 Hz, 3H); $^{13}$C NMR (CDCl$_3$) δ 164.7, 142.1, 122.7, 110.0, 69.9, 64.2, 36.3, 36.2, 31.9, 29.5(m), 28.3, 23.0, 22.8, 14.1 Anal. calcd for C$_{23}$H$_{39}$O$_5$Br C, 58.10; H, 8.23; Found C, 57.83; H, 8.41.

G. 2-(methyltetradecylamino)ethyl 3-(3,5,8-trioxa-4-tridecylbicyclo[2.2.2]octyl)prop-2-enoate 9.

To a solution of amine 8 (428 mg, 1.57 mmol) in THF (15 mL) at 0° C. was added n-butyl lithium (0.83 mL of a 2.15 M solution in hexane, 1.78 mmol). The resulting solution was stirred at 0° C. for 15 minutes whereupon a solution of the bromoethyl ortho ester (650 mg, 13.7 mmol) in THF (10 mL) at 0° C. was added via cannula. The reaction mixture was briefly stirred at 0° C. and then slowly allowed to warm to room temperature and stirred for 6 h. The reaction solvents were concentrated to one fourth the volume by rotary evaporation and the concentrate was diluted by addition of CH$_2$Cl$_2$. The mixture was washed with saturated NaHCO$_3$ and the organic layer was dried (Na$_2$SO$_4$). After removal of solvents, the residue was purified by silica gel column chromatography (NOTE: the SiO$_2$ must be pretreated by storing as a slurry in hexane containing 1% triethylamine), eluting with a gradient of 1–2.5% methanol in CH$_2$Cl$_2$ containing 1% triethylamine, to yield 550 mg (64.3%) of the ortho ester amine 9 as white solid. mp=55–56.8° C.; TLC (7.5% MeOH in CH$_2$Cl$_2$) R$_f$=0.50 IR (CHCl$_3$) 2917, 849, 1710, 1684, 1469 cm$^{-1}$ $^1$H NMR (CDCl$_3$) δ 6.55 (d, J=16.3 Hz, 1H), 5.70 (d, J=16.3 Hz, 1H), 4.22 (t, J=5.9 Hz, 2H), 4.04 (s, 6H), 2.64 (t, J=5.8 Hz, 2H), 2.37 (t, J=6 Hz, 2H), 2.26–2.34 (m, 5H), 1.68 (m, 2H), 1.40 (m, 2H), 1.25 (m, 42H), 0.88 (t, J=6.2 Hz, 6H); $^{13}$C NMR (CDCl$_3$) δ 165.3, 141.1, 123.5, 109.9, 70.1, 62.8, 58.1, 55.6, 42.7, 36.5, 36.1, 31.9, 29.6(m), 27.3, 27.2, 22.7, 14.0.

H. 2-(Methyltetradecylamino)ethyl 3-(3,5,8-trioxa-4-tridecylbicyclo[2.2.2]octyl propanoate 10.

To a solution of the unsaturated ortho ester 9 (550 mg, 0.88 mmol) in dry benzene (25 mL) at room temperature was added successively triethylamine (1 mL), 4 Å molecular sieves (ca. 100 mg) and 10% palladium on carbon (137 mg). The reaction was then fitted with a balloon containing hydrogen gas and stirred at room temperature for 3 h. The reaction mixture was filtered through a pad of Celite and the filtrate was concentrated to afford the crude product. Purification by silica gel column chromatography (NOTE: the SiO$_2$ must be pretreated by storing as a slurry in hexane containing 1% triethylamine), eluting with a gradient of 1–2.5% methanol in CH$_2$Cl$_2$ containing 1% triethylamine, afforded 500 mg (91%) of the ortho ester amine 10 as a colorless wax. TLC (7.5% MeOH in CH$_2$Cl$_2$) R$_f$=0.50 IR (CHCl$_3$) 2950,2852,1730, 1460 cm$^{-1}$; $^1$H NMR (CDCl$_3$) 4.15 (t, J=5.7 Hz, 2H), 3.89 (s, 6H), 2.58 (t, J=5.7 Hz, 2H), 2.45 (t, J=7.0 Hz, 2H), 2.24 (m, 5H), 1.61(m, 2H), 1.40 (m, 2H), 1.25 (m, 46H), 0.88 (t, J=5.6 Hz, 6H); $^{13}$C NMR (CDCl$_3$) δ 172.9, 109.7, 71.8, 71.1, 70.9, 63.0, 58.6, 56.0, 43.1, 37.0, 33.0, 32.2, 30.1(m), 28.5, 27.6, 25.1, 23.1, 14.5; HRMS(FAB) calc'd for C$_{38}$H$_{73}$NO$_5$ (M+H$^+$) 624.5566; found 624.5591.

Example 2

This Example illustrates the synthesis of the ammonium iodide salt (11) of the product of Example 1.
ZOE-1

In a sealed tube, the saturated amino ortho ester 10 (70 mg, 0.11 mmol) was dissolved in a large excess of iodomethane (1.5 mL, 24 mmol, pre-purified by passing through a short plug of basic alumina). The solution was purged with argon and stirred at room temperature for 3 hrs. The iodomethane was evaporated (NOTE: use a fume hood) and the residue was dissolved in CH$_2$Cl$_2$. Rotary evaporation of the solvent was performed to remove residual iodomethane and gave 86 mg (100%) of the ammonium iodide 11 as white powder, mp=162–165° C., IR (CHCl$_3$) 50,2852,1739,1468 cm$^{-1}$; $^1$H NMR (CDCl$_3$) δ 4.57 (m, 2H), 4.07 (m, 2H), 3.88 (s, 6H), 3.60 (m, 2H), 3.43 (s, 6H), 2.32 (t, J=7.3 Hz, 2H), 1.75 (m, 2H), 1.60 (m, 4H), 1.25 (m, 44H), 0.86 (t, J=5.5 Hz, 6H); $^{13}$C NMR (CDCl$_3$) δ 171.5, 109.1, 70.2, 65.7, 62.5, 57.8, 52.0, 36.5, 32.4, 31.8, 29.2, 28.0, 26.1, 24.2, 22.8, 22.5, 14.0; Anal. calcd for C$_{39}$H$_{76}$NO$_5$I C, 61.16; H, 10.00, N, 1.83. Found C, 61.23; H 10.09; N, 1.82.

ZOE-2 (see, FIG. 4)

A. (1-(hydroxymethyl)-3-oxetanyl)methyl octanoate (13).

Oxetane 2 (3 g, 25 mmol) was dried in vacuo at 100° C. for 1 h and then dissolved in THF (50 mL). To the solution at room temperature was added freshly distilled triethylamine (4.2 mL, 30 mmol) and N,N-(dimethylamino)pyridine (250 mg, 2 mmol) and the reaction was cooled to 0° C. Octanoyl chloride (3.5 mL, 20 mmol) was added via cannula to the reaction mixture, and the resulting yellowish solution was stirred at 0° C. for 4 h and then warmed to room temperature and stirred an additional 4 h. The reaction was quenched by addition of diethyl ether and washing with saturated aq. NaHCO$_3$, followed by washing with brine. The organic layer was separated and dried (Na$_2$SO$_4$). The solvents were removed by rotary evaporation, and the crude product was purified by silica gel column chromatography to yield 3.2 g (65%) of ester 13 as an oil; IR 3437, 1748, 1466 cm$^{-}$; $^1$H NMR δ 4.41–4.46 (m, 4H), 4.33 (s, 2H), 3.83 (d, J=5.7 Hz, 2H), 2.77 (t, J=5.7 Hz, 1H), 2.31 (t, J=7.4 Hz, 1H), 1.56–1.61 (m, 2H), 1.24 (m, 8H), 0.88 (t, J=4.5 Hz, 3H); $^{13}$C NMR δ 174.4, 75.8, 64.8, 63.8, 44.0, 34.1, 31.6, 29.0, 28.8, 24.9, 22.5, 14.0.

B. (1-Formyl-3-oxetanyl)methyl octanoate (14).

To a solution of oxalyl chloride (1.8 mL, 20.3 mmol) in CH$_2$Cl$_2$ (50 mL) at −78° C. was added dropwise dry DMSO (3.2 mL, 42 mmol). The resulting mixture was stirred at −78° C. for 15 minutes whereupon a solution of ester 13 (3.1 g, 12.7 mmol) in CH$_2$Cl$_2$ (10 mL) was added to slowly via cannula. After stirring at −78° C. for 1.5 hours, dry DIPEA (11.1 mL, 63.5 mmol) was add via syringe and the reaction was stirred at −78° C. an additional 30 mins. before warming to 0° C. and stirring for 10 mins. The reaction was diluted with CH$_2$Cl$_2$ and washed with 3% ammonium chloride (3×200 mL). The organic layer was separated dried (Na$_2$SO$_4$). After removal of the solvents, the crude solid was purified by silica gel column chromatography, eluting with a gradient of 25 to 50% ethyl acetate in hexane, to afford 2.4 g (78%) of aldehyde 14 as an oil; IR 2958, 2931, 2856, 1732, 1466 cm$^{-1}$; $^1$H NMR δ 9.89 (s, 1H), 4.83 (d, J=4.5 Hz, 2H), 4.56 (d, J=7.8 Hz, 4H), 2.29 (t, J=7.8 Hz, 2H), 1.59 (m, 2H), 1.30 (m, 8H), 0.85 (t, J=6.2 Hz, 3H); $^{13}$C NMR δ 198.1, 173.5, 72.7, 63.0, 50.3, 34.0, 31.6, 29.0, 28.8, 24.8, 22.5, 14.0.

C. 2-Bromoethyl 3-(1-(octanoyloxymethyl)-3-oxetanyl) prop-2-enoate (15).

To a solution of aldehyde 14 (2.0 g, 8.3 mmol) in THF (40 mL) at 0° C. was added triethylamine (11.5 mL, 83 mmol) and lithium bromide (2.9 g, 33 mmol). To the reaction mixture was then added a solution of the phosphonate reagent 5 (3.1 g, 10.3 mmol) in THF (10 mL) via cannula. The mixture was stirred at 0° C. for 0.5 h and then warmed to room temperature and stirred an additional 4 h. The reaction was diluted with diethyl ether and washed with brine, and the resulting organic layer was separated and dried (Na$_2$SO$_4$). The solvents were removed by rotary evaporation and the residue was purified by column chromatography, eluting with 20% ethyl acetate in hexane containing 1% triethyl amine, to obtain 2.40 g (74%) of the vinyl ester 15 as a colorless oil; IR 2924, 2854, 1734, 1654, 1467 cm$^{-1}$; $^1$H NMR δ 7.10 (d, J=16.1 Hz, 1H), 6.00 (d, J=16.1 Hz, 1H), 4.66–4.56 (m, 4H), 4.53 (t, J=6.1 Hz, 2H), 4.40 (s, 2H), 3.54 (t, J=6.1 Hz, 2H), 2.34 (t, J=7.4 Hz, 2H), 1.58 (m, 2H), 1.24 (m, 8H), 0.88 (t, J=5.5 Hz, 3H); $^{13}$C NMR δ 173.1, 165.0, 147.4, 121.1, 65.9, 63.7, 44.3, 33.7, 31.2, 28.7–28.1(m), 24.5, 22.2, 13.6.

D. 2-Bromoethyl 3-(3,5,8-trioxa-4-heptylbicyclo[2.2.2]octyl)prop-2-enoate (16).

To a solution of the vinyl ester 15 (1.5 g, 3.8 mmol) in CH$_2$Cl$_2$ (20 mL) at 0° C. was added boron trifluoride etherate (97 μL, 0.77 mmol). The reaction solution was gradually warmed to room temperature and stirred 12 h. The reaction was cooled to 0° C. and quenched by addition of triethylamine (0.53 mL, 3.8 mmol) and stirred 0.5 h. The mixture was diluted with Et$_2$O and filtered through a pad of Celite to remove the boron trifluoride·triethylamine complex. The filtrate was concentrated by rotary evaporation to yield the crude product which was purified by column chromatography (NOTE: the SiO$_2$ must be pretreated by storing as a slurry in hexane containing 1% triethylamine), eluting with a gradient of 25%–50% ethyl acetate in a hexane solution containing 1% triethylamine, to obtain 0.98 g (65%) of ortho ester 16 as white solid, mp=54.2–55.6° C.; IR 2921, 2850, 1718, 1654, 1469 cm$^{-1}$; $^1$H NMR δ 6.65 (d, J=16.3 Hz, 1H), 5.75 (d, J=16.3 Hz, 1H), 4.45 (t, J=6.1 Hz, 2H), 4.06 (s, 6 Hz), 3.53 (t, J=6.1 Hz, 2H), 1.63–1.70 (m, 2H), 1.44–1.40 (m, 2H), 1.24 (m, 8 Hz), 0.88 (t, J=6.7 Hz, 3H); $^{13}$C NMR δ 164.7, 142.1, 122.7, 110.0, 69.9, 64.2, 36.3, 36.2, 31.9, 29.5(m), 28.3, 23.0, 22.8, 14.1.

E. 2-(N-methyl-N-(2-hydroxyethyl)amino)ethyl 3-(3,5,8-trioxa-4-heptylbicyclo [2.2.2]octyl)prop-2-enoate (18).

To a solution N-methyldiethanolamine (17) (0.11 mL, 0.96 mmol) in THF (5 mL) at 0° C. was added n-butyl lithium (0.23 mL of a 2.47 M solution in hexane, 0.58 mmol). The resulting solution was stirred at 0° C. for 15 minutes whereupon a solution of the ortho ester 16 (150 mg, 0.38 mmol) in THF (5 mL) at 0° C. was added via cannula. The reaction mixture was briefly stirred at 0° C. and then slowly allowed to warm to room temperature and stirred for 6 h. The reaction solvents were concentrated to one fourth the volume by rotary evaporation and the concentrate was diluted by addition of CH$_2$Cl$_2$. The mixture was washed with saturated NaHCO$_3$ and the organic layer was dried (Na$_2$SO$_4$). After removal of solvents, the residue was purified by silica gel column chromatography (NOTE: the SiO$_2$ must be pretreated by storing as a slurry in hexane containing 1% triethylamine), eluting with a gradient of 2–5% methanol in CH$_2$Cl$_2$ containing 1% triethylamine, to yield 95 mg (64%) of the ortho ester amine 18 as colorless oil; TLC: 10% MeOH in CH$_2$Cl$_2$, R$_f$=0.3; IR (CHCl$_3$) 3469 (br), 2954, 2856, 1722, 1658, 1468 cm$^{-1}$; $^1$H NMR δ 6.55 (d, J=16.4 Hz, 1H), 5.75 (d, J=16.4 Hz, 1H), 4.20 (t, J=5.6 Hz, 2H), 4.05 (s, 6H), 3.52 (t, J=5.6 Hz, 2H), 2.70 (t, J=5.5 Hz, 2H), 2.55 (t, J=5.5 Hz, 2H), 2.33 (s, 3H), 1.65 (m, 2H), 1.57 (m,2H), 1.22 (m, 8H), 0.82 (t, J=4.3 Hz, 3H); $^{13}$C NMR δ 165.7, 141.4, 123.0, 109.7, 69.6, 62.3, 59.1, 58.3, 55.7, 42.0, 36.4, 36.0, 31.6, 29.3, 29.1, 22.9, 22.5, 14.0.

F. 2-(N-methyl-N-(2-tetradecanoyloxyethyl)amino)ethyl 3-(3,5,8-trioxa-4-heptyl bicyclo[2.2.2]octyl)prop-2-enoate (19).

To a solution of 18 (150 mg, 0.39 mmol) in CH$_2$Cl$_2$ (3.9 mL) at 0° C. was added freshly distilled triethylamine (0.17 mL, 1.17 mmol) and myristoyl chloride (0.12 mL, 0.43 mmol). The mixture was stirred 1 h at 0° C. and then warmed to room temperature overnight. The mixture was then diluted with CH$_2$Cl$_2$ and washed with saturated NaHCO$_3$. The organic layer was separated and dried (Na$_2$SO$_4$). After removal of solvents by rotary evaporation, the residue was purified by column chromatograph (NOTE: the silica gel must be pretreated by storing as slurry in hexane containing 1% triethyl amine), eluting with a gradient of 0–2% methanol in CH$_2$Cl$_2$ containing 1% triethylamine, to yield 205 mg (88%) of 19 as yellowish oil; TLC, 10% MeOH in CH$_2$Cl$_2$, R$_f$=0.65; IR 1732, 1657, 1468 cm$^{-1}$; $^1$H NMR δ 6.55 (d, J=16.4 Hz, 1H), 5.75 (d, J=16.4 Hz, 1H), 4.18 (t, J=5.6 Hz, 2H), 4.12 (t, J=5.9 Hz) 4.01 (s, 6H), 2.66 (m, 4H), 2.31 (s, 3H), 2.25 (t, J=7.6 Hz, 2H), 1.61–1.66 (m, 2H), 1.40–1.57 (m,4H), 1.22 (m, 24H), 0.82 (t, J=3.8 Hz, 6H); $^{13}$C NMR δ 173.1, 164.7, 140.8, 122.9., 109.5, 69.6, 62.22, 61.5, 55.6, 55.5, 42.5, 36.1, 36.0, 33.9, 31.4, 29.2(m), 24.5, 22.6, 22.4, 13.5.

G. 2-(N-methyl-N-(2-tetradecanoyloxyethyl)amino)ethyl 3-(3,5,8-trioxa-4-heptyl bicyclo[2.2.2]octyl) propanoate (20).

To a solution of the unsaturated ortho ester 19 (100 mg, 0.17 mmol) in dry benzene (3 mL) at room temperature was added successively triethylamine (0.1 mL), 4 Å molecular sieves (ca. 50 mg) and 10% palladium on carbon (20 mg). The reaction was then fitted with a balloon containing hydrogen gas and stirred at room temperature for 3h. The reaction mixture was filtered through a pad of Celite and the filtrate was concentrated to afford the crude product. Purification by silica gel column chromatography (NOTE: the SiO$_2$ must be pretreated by storing as a slurry in hexane containing 1% triethylamine), eluting with a gradient of 0–2.0% methanol in CH$_2$Cl$_2$ containing 1% triethylamine, afforded 92 mg (92%) of the ortho ester amine 20 as a colorless oil; TLC, 7.5% MeOH in CH$_2$Cl$_2$, R$_f$=0.60; IR 1734, 1468 cm$^{-1}$; $^1$H NMR δ 4.10–4.14 (m, 4H), 3.87 (s, 6H), 2.65 (m, 4H), 2.18–2.30 (m, 7H), 1.49–1.64 (m, 6H), 1.37–1.40 (m, 2H), 1.22 (m, 24H), 0.82 (m, 6H); $^{13}$C NMR δ 173.7, 172.3, 109.2, 72.3, 62.4, 61.8, 55.9, 55.8, 42.8, 36.5, 34.2, 32.5, 31.8, 31.7, 29.5(m), 28.0, 24.6, 24.5, 23.0, 22.6, 14.0; HRMS calc'd C$_{34}$H$_{63}$NO$_7$ 597.4604, found 597.4596.

H. N,N-dimethyl-N-(2-[3-(3,5,8-trioxa-4-heptylbicyclo [2.2.2]octyl)propanoyloxy]ethyl)-N-(2-tetradecanoyloxy) ethyl ammonium iodide (ZOE-2).

In a sealed tube, ortho ester 20 (50 mg, 0.083 mmol) was dissolved in large excess of iodomethane (1.5 mL, 24 mmol, pre-purified by passing through a short column of basic alumina). The solution was purged with argon and stirred at 0° C. for 3 h. The iodomethane then was evaporated (NOTE: use a well-ventilated fume hood) and the residue was dissolved in CH$_2$Cl$_2$. Rotary evaporation of the solvent was conducted to remove any residual iodomethane. In this manner, 61 mg (100%) of ZOE-2 was obtained as white powder, mp=92° C. (dec); IR 1738, 1468 cm$^{-1}$; $^1$H NMR δ 4.59 (m, 4H), 4.12 (m, 4H), 3.89 (s, 6H), 3.53 (s, 6H), 2.32–2.38 (m, 4H), 1.63–1.53 (m,6H), 1.30–1.22 (m, 26H), 0.82 (m, 6H); $^{13}$C NMR δ 172.6, 171.6, 109.2, 70.6, 63.9, 63.8, 57.9, 57.4, 52.9, 36.5, 34.0, 32.4, 31.8, 31.6, 29.0–29.5 (m), 28.1, 24.8, 24.6, 24.2, 23.0, 22.6, 22.5, 14.0.

I. Acid Hydrolysis Study

The following acid-hydrolysis experiment supports the proposed mechanism whereby acid exposure fragments the ortho ester lipid by forming a lactone.

With reference to FIG. 2, compound 10 (50 mg) was added to a mixture of 6 mL dioxane, 4 mL potassium biphthalate buffer (pH=4.50) and 15 mL deionized water. The pH was adjusted to pH=4.50 by addition of acetic acid. The mixture was stirred at 38° C. and monitored by thin layer chromatography. After complete hydrolysis (ca. 10 h), the reaction was neutralized by addition of solid sodium bicarbonate and diluted with dichloromethane. The organic layer was concentrated and the residue was separated by silica gel column chromatography (Note: the $SiO_2$ was pretreated with 1% triethylamine in hexane), eluting with a gradient of 1–5% methanol in dichloromethane containing 1% triethylamine. In this manner, lactone 12 and aminoalcohol 8 were isolated as the hydrolysis products.

J. 4-Hydroxymethyl-4-myristoyloxymethyl-5-hydroxypentanoic acid lactone (12)

mp=52.5–54.5° C.; IR ($CHCl_3$) 3436 (broad), 2900, 2850, 1743, 1467 $cm^{-1}$; $^1H$ NMR ($CDCl_3$) δ 4.17–4.10 (m, 4H), 3.48 (s, 2H), 2.55 (t, J=7.3 Hz, 2H), 2.33 (t, J=7.7 Hz, 2H), 1.74 (m, 2H), 1.61 (m, 2H), 1.25 (m, 20H), 0.87 (t, J=6.5 Hz, 3H); $^{13}C$ NMR ($CDCl_3$) δ 174.0, 172.3, 69.9, 67.1, 64.6, 63.4, 38.9, 34.1, 31.9, 29.2–29.1(m), 24.9, 23.7, 22.6, 14.0; HRMS (FAB): calcd for $C_{21}H_{38}O_5$ ($M^+H$) 371.2797, found 371.2781.

K. N-(2-Hydroxyethyl)-N-methyltetradecylamine (8)

$^1H$ NMR δ 3.55 (t, J=5.0 Hz, 2H), 2.95 (O$\underline{H}$, 1H), 2.55 (t, J=5.0 Hz, 2H), 2.42 (t, J=7.7 Hz, 2H), 2.25 (s, 3H), 1.45 (m, 2H), 1.23 (m, 22H), 0.80–0.76 (m, 3H); HRMS Calc'd $C_{17}H_{37}NO(M^+H)$ 272.2953, found 272.2948

Example 3

This Experiment illustrates liposome formulation and characterization using electron transmission microscopy.

Figure 7A:
FIGS. 7A–7B illustrate electron micrographs of (A) a liposome formulation of the present invention and (B) an enlargment.
Figure 7B:
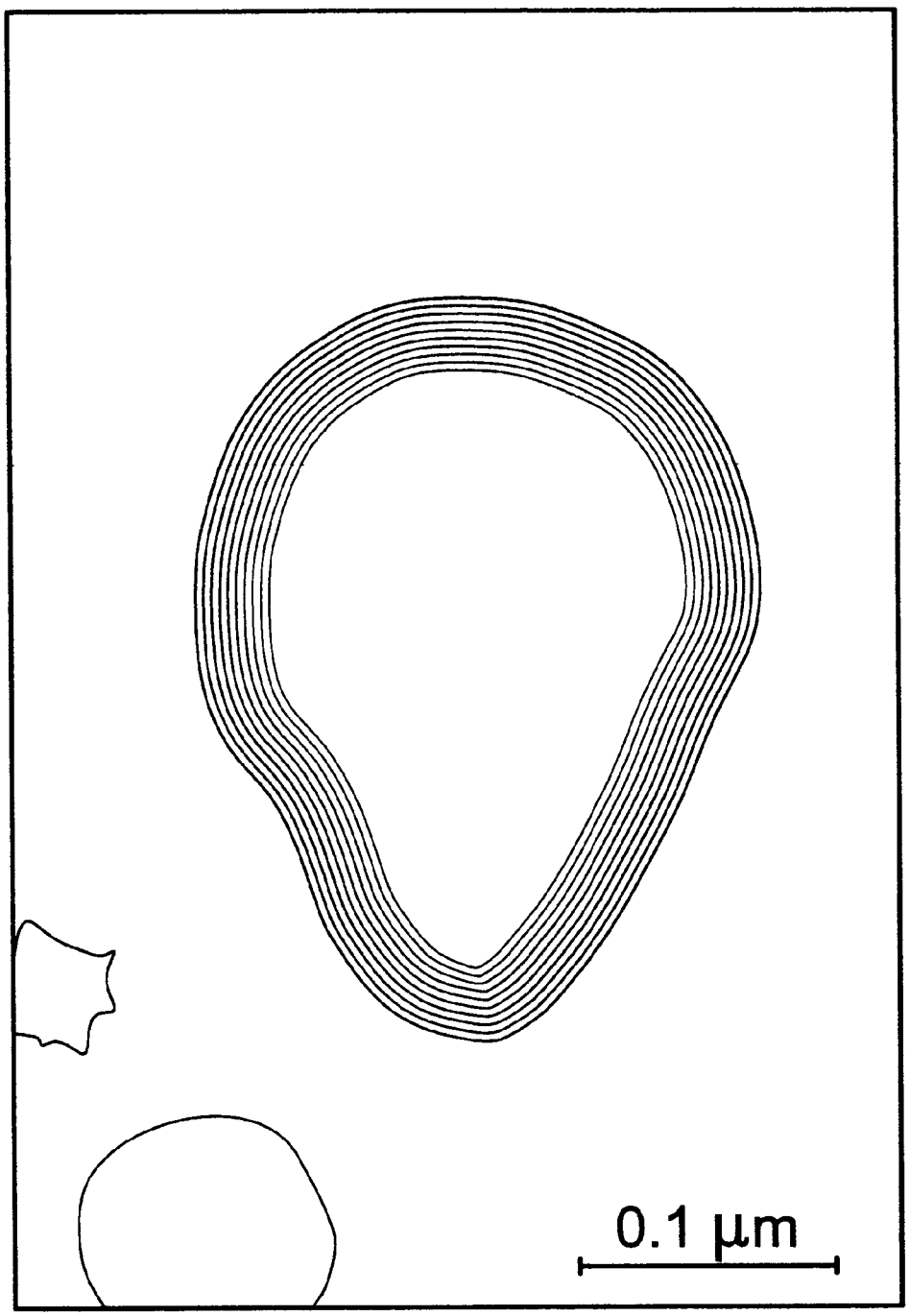

Cationic ortho ester lipid 11 was used to form liposomes. The electron micrograph data illustrates that the representative ortho ester lipid 11 forms vesicles on formulation in water. FIG. 7 suggests that the vesicles have multilamellar morphology.

A. Liposome Formulation.

Liposomes were prepared by mixing the ortho ester ammonium salt ZOE-1(1 μmol) with various amounts of 2,3-dioleoylphosphatidylethanolamine (DOPE) in chloroform in a vial to obtain formulations with molar ratios from 1:3 to 3:1 lipid:DOPE. The chloroform was removed by rotary evaporation, and the resultant lipid mixtures were dried in vacuo overnight to obtain lipid thin films. The films were hydrated with 1 mL PBS buffer (pH=7.40) to give 1 mM suspensions. The lipid suspensions were sonicated at 25° C. for 10 minutes using a bath-type sonicator (Laboratory Supplies Co., INC, Hicksville, N.Y.) to complete the liposome formulation.

B. Characterization Using Negative Staining Electron Microscopy.

An ortho ester liposome sample was prepared for analysis by transmission electron microscopy as follows: 10 μL of the liposome formulation (described above) was placed on formvar and carbon coated 400 mesh copper grids (Ted Pella, Inc. Redwood, Calif.). After 3–5 minutes, the grids were gently blotted near to dry with Whatman #1 filter paper and then 10 μL of 1% aqueous phosphotungstic acid (pH= 5.8) was added and allowed to stand for 3–5 minutes. After the aqueous phosphotungstic acid was blotted, the grids were allowed to dry at room temperature. The grids were viewed and photographed using a Philips EM 400 transmission electron microscope operated at 100 KV.

Example 4

This Experiment illustrates liposome formulation, entrapment and pH-induced release of the fluorescence probe calcein.

Figure 5A:
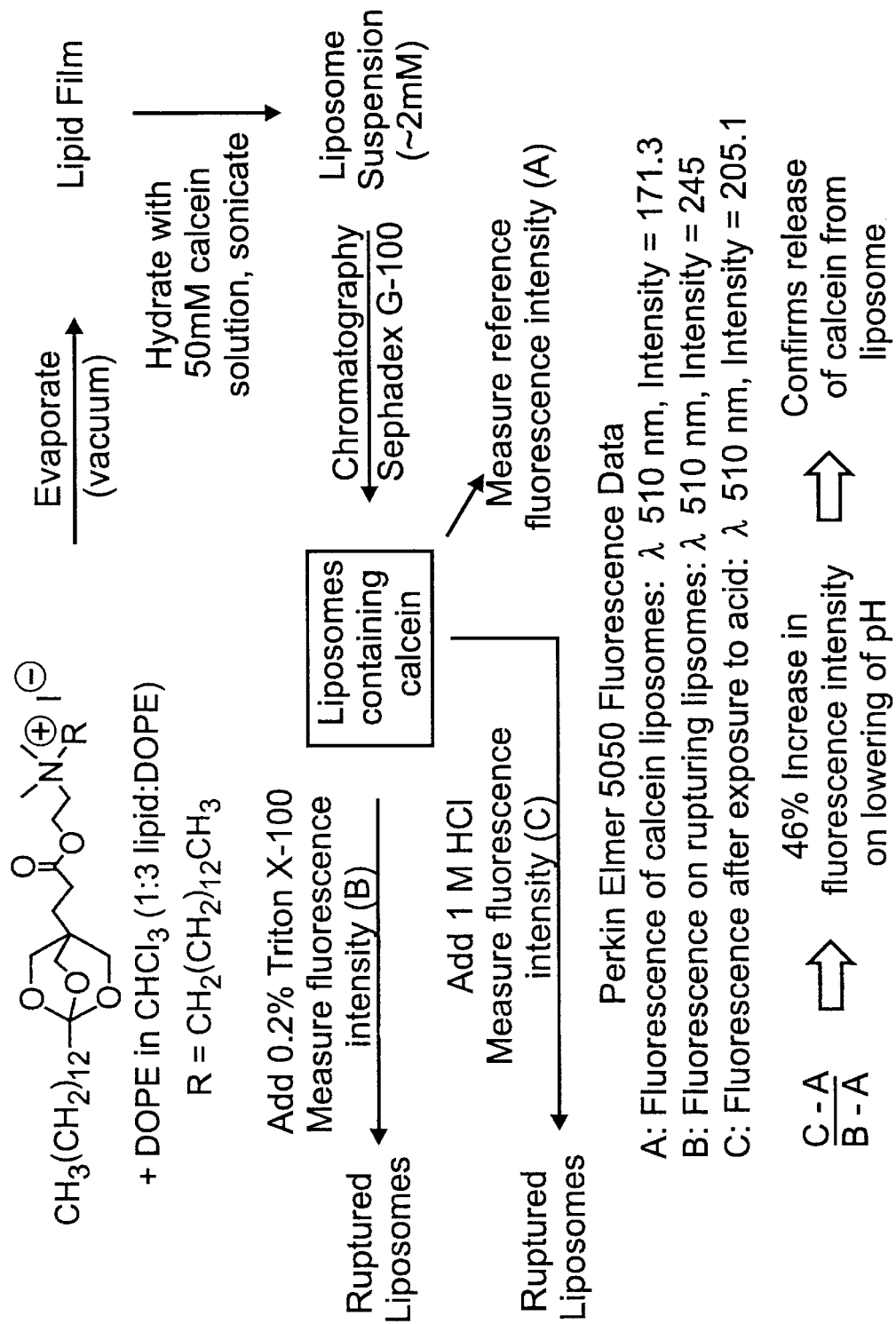
FIG. 5 A–B diagrammatically illustrates (A) liposome formulation, entrapment of a representative chemical agent and pH-induced release of an agent and (B) the chemical structure of calcein.
Figure 5B:
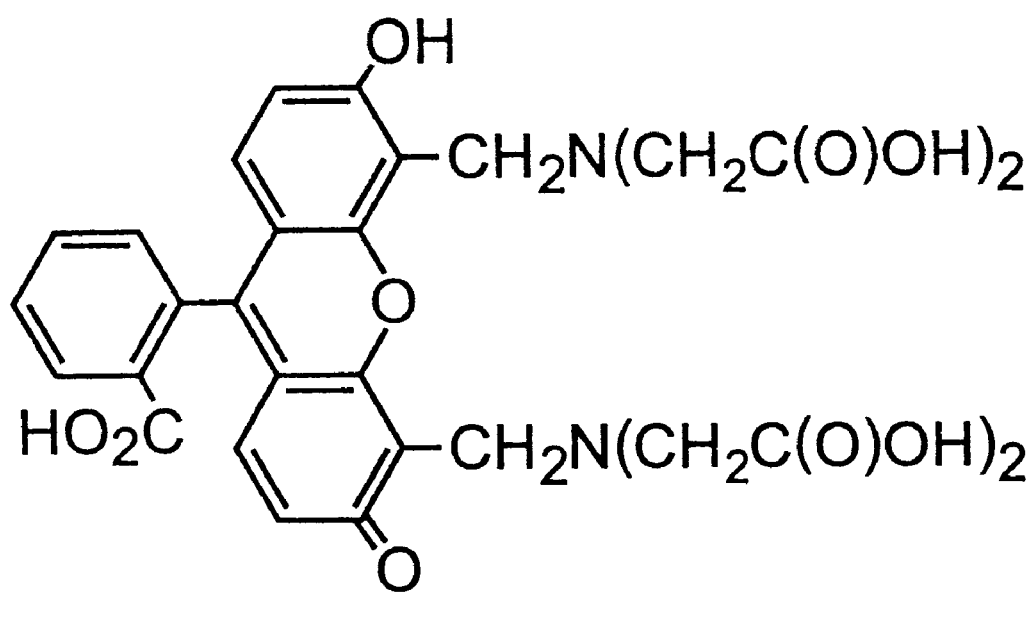

To illustrate that ortho ester lipids can be used to entrap contents and then release these contents on exposure to mild acidic conditions, a calcein fluorescence experiment was conducted (see, FIG. 5). To investigate the permeability of a cationic liposome preparation on lowering the pH, the liposomes containing the fluorescence probe calcein were exposed to aqueous buffer solution and then the pH of the solution was adjusted to mild acid condition while monitoring the fluorescence intensity. The rapid hydrolysis of the acid-vulnerable ortho ester of lipid 11 (ZOE-1) resulted in headgroup cleavage with concomitant liposome disruption. This was evidenced by the release of the entrapped calcein, a process that is accompanied by an increase in fluorescence emission. By monitoring the fluorescence intensity throughout the process, after 10 minutes of exposure to pH=3.5 conditions, there was a 46% increase in fluorescence intensity due to the calcein release from the ruptured liposomes. These results suggest that liposomes comprised of our pH-sensitive ortho ester construct can be used to entrap and deliver therapeutic agents, releasing the contents on exposure to acidic conditions.

A. Encapsulation of Calcein.

A thin film of ortho ester lipid and DOPE, prepared by mixing 2 μmol of the ortho ester ammonium lipid and 6 μmol DOPE, was dried in vacuo overnight. The dried film was then suspended in 1 mL PBS solution containing 50 mM calcein to give a suspension with a lipid concentration of 2 mM. The pH of the suspension was adjusted to pH=7.4 by addition of 1N NaOH. The suspension was vortex mixed and then sonicated for 20 minutes at room temperature using a bath sonicator (Laboratory supplies, Hicksville, N.Y.). Untrapped 'free' calcein was removed by gel filtration of the liposome suspension, accomplished by passing the suspension through Sephadex G-100 (Pharmacia Fine Chemical Inc, Piscataway, N.J.) while eluting with PBS solution. The liposome fractions (early fractions) were collected and used directly in the release study.

B. pH-Mediated Release of Entrapped Calcein.

A Perkin Elmer LS 50B luminescence spectrometer was used for the fluorescence assay. The excitation wavelength was 470 nm, and the excitation and emission slit width were 5 nm and 3 nm, respectively. A 25 μL liposome sample was aliquoted from a liposome fraction collected after Sephadex gel filtration and added to a cuvette containing 3 mL PBS. The relative fluorescence intensity was measured (A, FIG. 5) using the fluorescence spectrometer (value measured for A=F0=171.3, λ=512 nm). An appropriate amount of 1N HCl was then added to a portion of the same collected liposome fraction to achieve a pH=3.5. After stirring 10 mins at room temperature, a 25 μL aliquot was removed (C, FIG. 5) to measure the relative fluorescence intensity by addition to a cuvette containing 3 mL PBS (value measured for C=F1= 205.1, λ=512 nm).

As a control experiment, the liposomes were completely disrupted by adding 0.2% Trition X-100 (Aldrich chemical Co, Milwaukee, Wis.) to the original liposome fraction after gel filtration (B, FIG. 5). Measurement of the relative fluorescence on a 25 μL aliquot was performed in similar manner (value measured for B=F2=245.0, λ=512 nm). The percentage of liposome leakage was calculated using the following formula: Leakage percentage=(F1–F0)/(F2–F0)= 46%.

C. Comparison of Calcein Release from a DOTAP Liposome.

The control experiment was conducted following the same procedure using liposomes formulated from sonication of 1 mM DOTAP and DOPE (molar ratio 1:1). No leakage was observed for this comparison.

Example 5

This Example shows a study of DNA transfection using an ortho ester lipid of the present invention.

NIH 3T3 cells were transfected using two representative members of the novel ortho ester cationic lipid class. ZOE-1 and ZOE-2 (see, FIG. 6 for structures) both successfully delivered plasmid DNA encoding for the firefly enzyme luciferase.

A. Liposome Preparation

Liposomes were prepared either as unsonicated (unson.) or sonicated formulations. For either method, 1 μmol cationic lipid (ZOE-1 or ZOE-2) in chloroform was added to 1 μmol DOPE (Avanti Polar Lipids). After removing the solvent, the thin film was dried in vacuo overnight. The lipid mixture was suspended in 1 mL PBS buffer. For the unsonicated method, the suspension was vortex mixed for a few minutes and then used directly. For the sonicated method, the lipid suspension was sonicated at room temperature for 10 minutes using a bath sonicator.

B. Transfection of Cultured Cell Lines

The NIH 3T3 cell line was plated on 24-well tissue culture plates. The growth media were removed via aspiration and the cells were washed with 0.5 mL PBS buffer twice. The liposome-DNA complexes were formed through sequential addition of appropriate amount of serum free media, liposome formulation and PGL-3 control DNA into a 2 mL Eppendorf tube to a total volume of 800 μL. Typically, 18 μL lipid emulsion was used to complex 4 μg DNA to yield 1.5:1 positive to negative charge ratio. The addition of these substances was followed by rapid vortex mixing and centrifuging. 200 μL of the resulting complex was added to each well (1 μg PGL-3 DNA/well) and the cells were incubated 4 hrs at 37° C. At this time, 500 μL medium containing 10% FBS was added to each well. The cells were harvested 48 hrs before lysis and analysis.

C. Luciferase Assay

Relative luciferase activity was determined by using the enhanced luciferase assay kit and monolight 2010 luminiometer (from Analytical Luminescence Laboratory, San Diego, Calif.). 233.3 μL of concentrated luciferase lysis buffer was added to each well and the cells were then placed on ice for at least 30 minutes. The total volume in each well before analysis was 933.3 μL and the luciferase light emission from 31.1 μL out of total volume was measured over 10 seconds. The result was expressed as a function of the total 933.3 μL and are illustrated in FIG. 8.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula

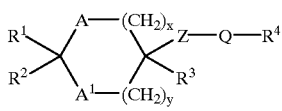

I wherein:

$R^1$ is a member selected from the group consisting of optionally substituted $(C_7-C_{17})$alkyl, optionally substituted $(C_7-C_{17})$alkenyl and optionally substituted $(C_7-C_{17})$alkynyl;

$R^2$ is a member selected from the group consisting of $(C_1-C_{18})$alkoxy and $(C_1-C_{18})$alkylthio;

$R^3$ is hydrogen; alternatively, $R^2$ and $R^3$ and the carbons to which they are bound join to form a 5,6-membered; a 6,6-membered; a 6,7-membered; or a 7,7-membered bicyclic ortho ester or ortho thioester ring;

A and $A^1$ are members independently selected from the group consisting of oxygen and sulfur;

x and y are independently selected from the integers 0, 1 and 2;

Z is a member selected from the group consisting of optionally substituted alkylene, optionally substituted alkyleneoxyalkylene and optionally substituted alkyleneaminoalkylene;

Q is a member selected from the group consisting of carboxyl, thiocarboxyl, dithiocarboxyl, carbonate, carbamate, phospho, phosphothio, phosphoro and thiophosphoro; and $R^4$ is a nitrogen containing headgroup wherein the nitrogen can be unsubstituted, mono-substituted, di-substituted, or a quaternary nitrogen salt and wherein the nitrogen substituent(s) are member(s) independently selected from the group consisting of optionally substituted $(C_1-C_{18})$alkyl, optionally substituted $(C_1-C_{18})$alkenyl, and optionally substituted $(C_1-C_{18})$alkynyl and wherein $R^4$ and Q are optionally linked with a $(C_1-C_5)$alkylene or $(C_2-C_5)$alkenyl group.

2. The compound of claim 1, wherein:

$R^1$ is a member selected from the group consisting of $(C_7-C_{17})$alkyl and substituted $(C_7-C_{17})$alkyl;

$R^2$ and $R^3$ and the carbons to which they are bound join to form a 6,6-membered; a 6,7-membered; or a 7,7-membered bicyclic ortho ester ring;

A and $A^1$ are oxygen;

x and y are independently selected from the integers 0, 1 and 2;

Z is optionally substituted alkylene;

Q is a member selected from the group consisting of carboxyl, phospho, and phosphoro;

$R^4$ is a member selected from the group consisting of optionally substituted amino$(C_1-C_5)$alkylene, optionally substituted $(C_1-C_{18})$alkylamino$(C_1-C_5)$alkylene, optionally substituted $(C_1-C_{18})$alkoylamino$(C_2-C_5)$alkenyl, optionally substituted $(C_1-C_{18})$dialkylamino$(C_1-C_5)$alkylene, optionally substituted $(C_1-C_{18})$dialkylamino$(C_2-C_5)$alkenyl, and a quaternary nitrogen salt having the structure

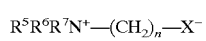

wherein:

$R^5$, $R^6$ and $R^7$ are members independently selected from the group consisting of hydrogen, optionally substituted $(C_1-C_{18})$alkyl, optionally substituted $(C_2-C_{18})$alkenyl and optionally substituted $(C_2-C_{18})$alkynyl;

n is an integer from 1 to 5 inclusive; and

X is a member selected from the group consisting of chloride, iodide, fluoride and bromide.

3. The compound of claim 1, having the formula

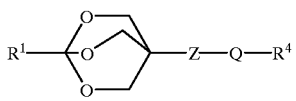

II wherein:
$R^1$ is a member selected from the group consisting of $(C_7–C_{17})$alkyl and substituted $(C_7–C_{17})$alkyl;
Z is optionally substituted alkylene;
Q is carboxyl;
$R^4$ is a member selected from the group consisting of optionally substituted $(C_1–C_{18})$alkylamino$(C_1–C_5)$alkylene, optionally substituted $(C_1–C_{18})$dialkylamino$(C_1–C_5)$alkylene and a quaternary nitrogen salt having the structure

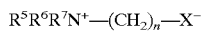

wherein: $R^5$, $R^6$ and $R^7$ are members independently selected from the group consisting of hydrogen, optionally substituted $(C_1–C_{18})$alkyl, optionally substituted $(C_2–C_{18})$alkenyl and optionally substituted $(C_2–C_{18})$alkynyl;
n is an integer from 1 to 5 inclusive; and
X is a member selected from the group consisting of chloride, iodide, fluoride and bromide.

4. The compound of claim 3, wherein:
$R^1$ is $(C_7–C_{17})$alkyl optionally substituted with one or more members selected from the group consisting of lower alkyl, acyl, halogen, hydroxy, amino, alkoxy, alkylamino, acylamino, acyloxy, and mercapto;
Z is $(C_1–C_3)$ alkylene optionally substituted with one or more members selected from the group consisting of lower alkyl, aryl, acyl, halogen, hydroxy, amino, alkoxy, alkylamino, acylamino, acyloxy, aryloxy, aryloxyalkyl, mercapto, both saturated and unsaturated cyclic hydrocarbons and heterocycles;
$R^4$ is a member selected from the group consisting of optionally substituted $(C_1–C_{18})$alkylamino$(C_1–C_5)$alkylene or optionally substituted $(C_1–C_{18})$dialkylamino$(C_1–C_5)$alkylene, wherein the substituent is one or members selected from the group consisting of lower alkyl, aryl, acyl, halogen, hydroxy, amino, alkoxy, alkylamino, acylamino, acyloxy, aryloxy, aryloxyalkyl, mercapto, both saturated and unsaturated cyclic hydrocarbons and heterocycles; and
an ammonium salt having the structure:

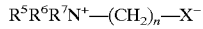

wherein:
$R^5$ is methyl;
$R^6$ and $R^7$ are members independently selected from the group consisting of hydrogen, optionally substituted $(C_1–C_{18})$alkyl and optionally substituted $(C_2–C_{18})$alkenyl;
n is 2; and
X is iodide.

5. The compound of claim 4, wherein:
$R^1$ is $(C_7–C_{17})$alkyl optionally substituted with $(C_7–C_{18})$acyloxy;
Z is $(C_1–C_3)$ alkylene optionally substituted with $(C_7–C_{18})$alkoxy; and $R^4$ is a member selected from the group consisting of optionally substituted $(C_1–C_{18})$alkylamino$(C_1–C_5)$alkylene, optionally substituted $(C_1–C_{18})$dialkylamino$(C_1–C_5)$alkylene wherein the substituent is $(C_1–C_{18})$acyloxy, and an ammonium salt wherein:
$R^6$ is methyl.

6. The compound of claim 3, wherein:
$R^1$ is a $(C_{13}–C_{17})$alkyl;
Z is $(C_1–C_3)$alkylene;
$R^4$ is a member selected from the group consisting of $(C_{14}–C_{18})$acyloxy$(C_1–C_5)$alkylamino$(C_2–C_4)$alkylene and an ammonium salt wherein:
$R^5$ and $R^6$ are both methyl; and
$R^7$ is $(C_{14}–C_{18})$acyloxy$(C_1–C_5)$alkylene.

7. The compound of claim 3, wherein:
$R^1$ is $(C_{14})$alkyl;
Z is $(C_2)$alkylene; and
$R^4$ is a member selected from the group consisting of $(C_{14})$alkylamino$(C_2)$alkylene and an ammonium salt wherein:
$R^5$ and $R^6$ are both methyl; and
$R^7$ is $(C_{14})$alkyl.

8. The compound of claim 3, wherein:
$R^1$ is $(C_{14})$alkyl;
Z is $(C_2)$alkylene; and
$R^4$ is a member selected from the group consisting of N-methyl-N-(tetradecanyl)amino$(C_2)$alkylene and an ammonium salt thereof wherein:
$R^5$ and $R^6$ are both methyl; and
$R^7$ is $(C_{14})$alkyl.

9. The compound of claim 5, wherein:
$R^1$ is $(C_{14})$acyloxy$(C_{13})$alkyl.

10. The compound of claim 5, wherein:
$R^4$ is a member selected from the group consisting of $(C_{15})$acyloxy$(C_2)$alkyleneamino$(C_2)$alkylene; and an ammonium salt wherein:
$R^7$ is $(C_{15})$acyloxy$(C_2)$alkylene.

11. The compound of claim 3, wherein: said compound is N,N-dimethyl-N-tetradecyl-N-(2-[3-(3,5,8-trioxa-4-tridecylbicyclo[2.2.2]octyl)propanoyloxy]ethyl) ammonium iodide.

12. The compound of claim 3, wherein: said compound is (N,N-dimethyl-N-(2-[3-(3,5,8-trioxa-4-heptylbicyclo[2.2.2]octyl)propanoyloxy]ethyl)-N-(2-tetradecanoyloxy)ethyl ammonium iodide.

13. A lipid formulation comprising a compound of the formula

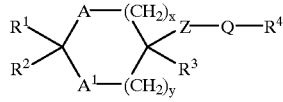

I wherein:
$R^1$ is a member selected from the group consisting of optionally substituted $(C_7–C_{17})$alkyl, optionally substituted $(C_7–C_{17})$alkenyl and optionally substituted $(C_7–C_{17})$alkynyl;
$R^2$ is a member selected from the group consisting of $(C_1–C_{18})$alkoxy and $(C_1–C_{18})$alkylthio;
$R^3$ is hydrogen; alternatively,
$R^2$ and $R^3$ and the carbons to which they are bound join to form a 5,6-membered; a 6,6-membered; a 6,7- membered; or a 7,7-membered bicyclic ortho ester or ortho thioester ring;

A and $A^1$ are members independently selected from the group consisting of oxygen and sulfur;

x and y are independently selected from the integers 0, 1 and 2;

Z is a member selected from the group consisting of optionally substituted alkylene, optionally substituted alkyleneoxyalkylene and optionally substituted alkyleneaminoalkylene;

Q is a member selected from the group consisting of carboxyl, thiocarboxyl, dithiocarboxyl, carbonate, carbamate, phospho, phosphothio, phosphoro and thiophosphoro; and $R^4$ is a nitrogen containing headgroup wherein the nitrogen can be unsubstituted, mono-substituted, di-substituted, or a quaternary nitrogen salt and wherein the nitrogen substituent(s) are member(s) independently selected from the group consisting of optionally substituted $(C_1-C_{18})$alkyl, optionally substituted $(C_1-C_{18})$alkenyl, and optionally substituted $(C_1-C_{18})$alkynyl and wherein $R^4$ and Q are optionally linked with a $(C_1-C_5)$alkylene or $(C_2-C_5)$alkenyl group; and a bioactive agent.

14. The lipid formulation of claim 13, wherein said bioactive agent is a nucleic acid.

15. The lipid formulation of claim 13, wherein said compound is formulated into a liposome.

16. The lipid formulation of claim 13, wherein said compound has the formula:

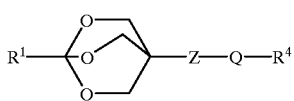

II wherein:

$R^1$ is a member selected from the group consisting of $(C_7-C_{17})$alkyl and substituted $(C_7-C_{17})$alkyl;

Z is optionally substituted alkylene;

Q is carboxyl;

$R^4$ is a member selected from the group consisting of optionally substituted $(C_1-C_{18})$alkylamino$(C_1-C_5)$alkylene, optionally substituted $(C_1-C_{18})$dialkylamino$(C_1-C_5)$alkylene and a quaternary nitrogen salt having the structure $R^5R^6R^7N^+$—$(CH_2)_n$—$X^-$ wherein: $R^5$, $R^6$ and $R^7$ are members independently selected from the group consisting of hydrogen, optionally substituted $(C_1-C_{18})$alkyl, optionally substituted $(C_2-C_{18})$alkenyl and optionally substituted $(C_2-C_{18})$alkynyl;

n is an integer from 1 to 5 inclusive; and

X is a member selected from the group consisting of chloride, iodide, fluoride and bromide.

17. The lipid formulation of claim 16, wherein:

$R^1$ is $(C_7-C_{17})$alkyl optionally substituted with one or more members selected from the group consisting of lower alkyl, acyl, halogen, hydroxy, amino, alkoxy, alkylamino, acylamino, acyloxy, and mercapto;

Z is $(C_1-C_3)$ alkylene optionally substituted with one or more members selected from the group consisting of lower alkyl, aryl, acyl, halogen, hydroxy, amino, alkoxy, alkylamino, acylamino, acyloxy, aryloxy, aryloxyalkyl, mercapto, both saturated and unsaturated cyclic hydrocarbons and heterocycles;

$R^4$ is a member selected from the group consisting of optionally substituted $(C_1-C_{18})$alkylamino$(C_1-C_5)$alkylene or optionally substituted $(C_1-C_{18})$dialkylamino$(C_1-C_5)$alkylene, wherein the substituent is one or more members selected from the group consisting of lower alkyl, aryl, acyl, halogen, hydroxy, amino, alkoxy, alkylamino, acylamino, acyloxy, aryloxy, aryloxyalkyl, mercapto, both saturated and unsaturated cyclic hydrocarbons and heterocycles; and an ammonium salt having the structure:

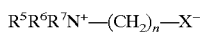

wherein:

$R^5$ is methyl;

$R^6$ and $R^7$ are members independently selected from the group consisting of hydrogen, optionally substituted $(C_1-C_{18})$alkyl and optionally substituted $(C_2-C_{18})$alkenyl;

n is 2; and

X is iodide.

18. The lipid formulation of claim 17, wherein:

$R^1$ is $(C_7-C_{17})$alkyl optionally substituted with $(C_7-C_{18})$acyloxy;

Z is $(C_1-C_3)$ alkylene optionally substituted with $(C_7-C_{18})$alkoxy; and $R^4$ is a member selected from the group consisting of optionally substituted $(C_1-C_{18})$alkylamino$(C_1-C_5)$alkylene, optionally substituted $(C_1-C_{18})$dialkylamino$(C_1-C_5)$alkylene wherein the substituent is $(C_1-C_{18})$acyloxy, and an ammonium salt wherein:

$R^6$ is methyl.

19. The lipid formulation of claim 17, wherein:

$R^1$ is a $(C_{14}-C_{17})$alkyl;

Z is $(C_1-C_3)$alkylene;

$R^4$ is a member selected from the group consisting of $(C_{14}-C_{18})$acyloxy$(C_1-C_5)$alkylamino$(C_2-C_4)$alkylene and an ammonium salt wherein:

$R^6$ is methyl; and $R^7$ is $(C_{14}-C_{18})$acyloxy$(C_1-C_5)$alkylene.

20. The lipid formulation of claim 17, wherein:

$R^1$ is $(C_{13})$alkyl;

Z is $(C_2)$alkylene; and $R^4$ is a member selected from the group consisting of N-methyl-N-(tetradecanyl)amino$(C_2)$alkylene and an ammonium salt thereof wherein:

$R^6$ is methyl; and $R^7$ is $(C_{14})$alkyl.

21. The lipid formulation of claim 17, wherein:

$R^1$ is $(C_{14})$acyloxy$(C_{13})$alkyl.

22. The lipid formulation of claim 17, wherein:

$R^4$ is a member selected from the group consisting of $(C_{15})$acyloxy$(C_2)$alkyleneamino$(C_2)$alkylene; and an ammonium salt wherein:

$R^7$ is $(C_{15})$acyloxy$(C_2)$alkylene.

23. A method for transfecting a cell, said method comprising:

contacting said cell with a lipid formulation comprising a compound of the formula

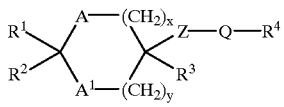

wherein:
- $R^1$ is a member selected from the group consisting of optionally substituted ($C_7$–$C_{17}$)alkyl, optionally substituted ($C_7$–$C_{17}$)alkenyl and optionally substituted ($C_7$–$C_{17}$)alkynyl;
- $R^2$ is a member selected from the group consisting of ($C_1$–$C_{18}$)alkoxy and ($C_1$–$C_{18}$)alkylthio;
- $R^3$ is hydrogen; alternatively,
- $R^2$ and $R^3$ and the carbons to which they are bound join to form a 5,6-membered; a 6,6-membered; a 6,7-membered; or a 7,7-membered bicyclic ortho ester or ortho thioester ring;
- A and $A^1$ are members independently selected from the group consisting of oxygen and sulfur;
- x and y are independently selected from the integers 0, 1 and 2;
- Z is a member selected from the group consisting of optionally substituted alkylene, optionally substituted alkyleneoxyalkylene and optionally substituted alkyleneaminoalkylene;
- Q is a member selected from the group consisting of carboxyl, thiocarboxyl, dithiocarboxyl, carbonate, carbamate, phospho, phosphothio, phosphoro and thiophosphoro; and
- $R^4$ is a nitrogen containing headgroup wherein the nitrogen can be unsubstituted, mono-substituted, di-substituted, or a quaternary nitrogen salt and wherein the nitrogen substituent(s) are member(s) independently selected from the group consisting of optionally substituted ($C_1$–$C_{18}$)alkyl, optionally substituted ($C_1$–$C_{18}$)alkenyl, and optionally substituted ($C_1$–$C_{18}$)alkynyl and wherein $R^4$ and Q are optionally linked with a ($C_1$–$C_5$)alkylene or ($C_2$–$C_5$)alkenyl group; and a nucleic acid, thereby transfecting said cell.

24. The method of claim 23, wherein said lipid formulation comprises a liposome.

25. A method for delivering a bioactive agent to a cell, said method comprising:
contacting said cell with a lipid formulation comprising a compound of the formula

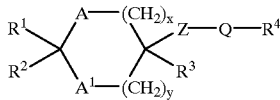

wherein:
- $R^1$ is a member selected from the group consisting of optionally substituted ($C_7$–$C_{17}$)alkyl, optionally substituted ($C_7$–$C_{17}$)alkenyl and optionally substituted ($C_7$–$C_{17}$)alkynyl;
- $R^2$ is a member selected from the group consisting of ($C_1$–$C_{18}$)alkoxy and ($C_1$–$C_{18}$)alkylthio;
- $R^3$ is hydrogen; alternatively,
- $R^2$ and $R^3$ and the carbons to which they are bound join to form a 5,6-membered; a 6,6-membered; a 6,7-membered; or a 7,7-membered bicyclic ortho ester or ortho thioester ring;
- A and $A^1$ are members independently selected from the group consisting of oxygen and sulfur;
- x and y are independently selected from the integers 0, 1 and 2;
- Z is a member selected from the group consisting of optionally substituted alkylene, optionally substituted alkyleneoxyalkylene and optionally substituted alkyleneaminoalkylene;
- Q is a member selected from the group consisting of carboxyl, thiocarboxyl, dithiocarboxyl, carbonate, carbamate, phospho, phosphothio, phosphoro and thiophosphoro; and
- $R^4$ is a nitrogen containing headgroup wherein the nitrogen can be unsubstituted, mono-substituted, di-substituted, or a quaternary nitrogen salt and wherein the nitrogen substituent(s) are member(s) independently selected from the group consisting of optionally substituted ($C_1$–$C_{18}$)alkyl, optionally substituted ($C_1$–$C_{18}$)alkenyl, and optionally substituted ($C_1$–$C_{18}$) alkynyl and wherein $R^4$ and Q are optionally linked with a ($C_1$–$C_5$)alkylene or ($C_2$–$C_5$)alkenyl group; and a bioactive agent, thereby delivering said bioactive agent to said cell.

26. The method of claim 25, wherein said bioactive agent is a member selected from the group consisting of antimicrobials, antibiotics, antimyobacterials, antifungals, antivirals, neoplastic agents, agents affecting the immune response, blood calcium regulators, agents useful in glucose regulation, anticoagulants, antithrombotics, antihyperlipidemic agents, cardiac drugs, thyromimetic drugs, antithyroid drugs, adrenergics, antihypertensive agents, cholinergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, antiarthritics, diagnostic agents, antineoplastic agents and anti-infective agents.

27. The method of claim 25, wherein said bioactive agent is a small molecule.

28. The method of claim 25, wherein said lipid formulation is a liposome.

* * * * *